(12) United States Patent
Back et al.

(10) Patent No.: US 11,091,417 B2
(45) Date of Patent: Aug. 17, 2021

(54) PROCESS FOR THE DECARBOXYLATIVE KETONIZATION OF FATTY ACIDS OR FATTY ACID DERIVATIVES

(71) Applicant: RHODIA OPERATIONS, Paris (FR)

(72) Inventors: Olivier Back, Lyons (FR); Rémy Leroy, Mions (FR); Philippe Marion, Vernaison (FR)

(73) Assignee: RHODIA OPERATIONS, Aubervilliers (FR)

( * ) Notice: Subject to any disclaimer, the term of this patent is extended or adjusted under 35 U.S.C. 154(b) by 248 days.

(21) Appl. No.: 16/326,460

(22) PCT Filed: Aug. 17, 2017

(86) PCT No.: PCT/EP2017/070884
§ 371 (c)(1),
(2) Date: Feb. 19, 2019

(87) PCT Pub. No.: WO2018/033607
PCT Pub. Date: Feb. 22, 2018

(65) Prior Publication Data
US 2021/0024443 A1      Jan. 28, 2021

(30) Foreign Application Priority Data

Aug. 19, 2016   (EP) .................................. 16306069
Nov. 8, 2016    (EP) .................................. 16306470

(51) Int. Cl.
C07C 45/48   (2006.01)

(52) U.S. Cl.
CPC .................................. *C07C 45/48* (2013.01)

(58) Field of Classification Search
CPC .................................................. C07C 45/48
See application file for complete search history.

(56) References Cited

U.S. PATENT DOCUMENTS

| | | |
|---|---|---|
| 3,646,100 A | 2/1972 | Sherman et al. |
| 3,646,106 A | 2/1972 | Carr et al. |
| 3,976,697 A | 8/1976 | Kuntschik et al. |
| 4,950,763 A | 8/1990 | Schommer et al. |
| 8,927,796 B2 * | 1/2015 | Miller ...................... C10G 3/50 585/240 |
| 9,193,653 B1 | 11/2015 | Hommeltoft |
| 10,035,746 B2 | 7/2018 | Back et al. |
| 2014/0335586 A1 | 11/2014 | Zhang et al. |

FOREIGN PATENT DOCUMENTS

| | | |
|---|---|---|
| DE | 295657 C | 12/1916 |
| EP | 2468708 A | 6/2012 |

OTHER PUBLICATIONS

Gooßen, L. J., et al., "Catalytic Decarboxylative Cross-Ketonisation of Aryl- and Alkylcarboxylic Acids using Magnetite Nanoparticles", Adv. Synth. Catal. (2011) 353, pp. 57-63.
Klimkiewicz, R., et al., "Oil Industry Waste as a Basis for Synthesis of New Type Surfactants", Polish Journal of Environmental Studies vol. 10, No. 5 (2001), pp. 337-339.
Curtis, et al., "The Ketonization of Higher Fatty Acids with Some Observations on the Mechanism of the Reaction Part I. Studies of Waxes", Journal of the Society of Chemical Industry (1947) 66, pp. 402-407.
F. Chemla et al, "High Kinetic Resolution in the Addition of a Racemic Allenylzinc onto Enantiopure N-tert-Butanesulfinimines: Concise Synthesis of Enantiopure trans-2-Ethynylaziridines", Journal of Organic Chemistry, 2004, 69, 8244-8250 (7 pages).
M. Krämer et al, "pH-Responsive Molecular Nanocarriers Based on Dendritic Core-Shell Architectures", Angew. Chem. Int. Ed., 2002, 41, No. 22 (5 pages).
Office Action issued in European Application No. 17752145.7, dated Sep. 7, 2020 (5 pages).
Office Action issued in Russian Application No. 2019107581/04(014723), dated Nov. 13, 2020 (26 pages).

* cited by examiner

*Primary Examiner* — Sikarl A Witherspoon
(74) *Attorney, Agent, or Firm* — Osha Bergman Watanabe & Burton LLP

(57) ABSTRACT

The present invention is directed to a process for synthesizing an internal ketone K1 by decarboxylative ketonization reaction of a fatty acid, a fatty acid derivative or a mixture thereof in a liquid phase with a metal compound as catalyst in a reaction medium, said process being characterized in that a ketone K2 at liquid state, which is identical or similar to the ketone K1, is introduced into the reaction medium. The so-synthesized internal ketone K1 can be used for the preparation of a variety of end compounds, including surfactants having a twin-tail structure or a Gemini structure.

25 Claims, No Drawings

PROCESS FOR THE DECARBOXYLATIVE KETONIZATION OF FATTY ACIDS OR FATTY ACID DERIVATIVES

CROSS-REFERENCE TO RELATED APPLICATIONS

This application is a U.S. national stage entry under 35 U.S.C. § 371 of International Application No. PCT/EP2017/070884 filed Aug. 17, 2017, which claims priority to European application No. 16306069.2, filed on Aug. 19, 2016, and European application No. 16306470.2, filed on Nov. 8, 2016. The entire contents of these applications are explicitly incorporated herein by this reference.

The present invention relates to a process for the manufacture of internal ketones through decarboxylative ketonization of long chain fatty acids or derivatives of fatty acids.

The present invention further relates to a method for the preparation of end compounds starting from the so-manufactured long chain internal ketones.

Finally, the present invention relates to the end compounds susceptible of being prepared by this method.

The conversion of acids into respective ketones by decarboxylative ketonization is a well-known process which is already commercially used.

The process can be carried out in the gas phase at temperatures usually exceeding 350° C. and usually above 400° C. for fatty acids in the presence of catalytic amounts of metal oxide compounds (e.g. MgO, ZrO2, Al2O3, CeO2, MnO2, TiO2).

Carrying out the reaction in the gas phase with fatty acids with a high boiling point is difficult as the evaporation of the reactants needs very high temperatures which are detrimental for the selectivity of the process and leads to the formation of undesired by-products.

In US 2014/335586 A, the reaction is carried out with medium-chain fatty acids (MCFAs). Thus, a feed of fatty acids having from 4 to 9 carbon atoms is mixed with some recycled ketone product having from 7 to 17 carbon atoms, and preheated to 300-400° C. before being fed to a fixed bed reactor packed with a metal oxide catalyst, typically with 20 percent MnO2 or CeO2 on alumina support. The reactor outflow is cooled down before being sent to a three phase separator. The vapor phase (comprising mostly $CO_2$) is vented, while the water phase may be removed from the bottom.

Carrying out the process in the liquid phase offers certain advantages over the reaction in the gas phase, e.g. usually higher productivities, better selectivity which is important for the subsequent work-up of the reaction mixture and finally allows getting reduced manufacturing costs.

In prior art liquid phase reaction processes, metals are usually employed in stoichiometric amounts to carry out the reaction. The reaction goes through the formation of metallic carboxylate salts which decompose to ketone and $CO_2$.

German patent DE 295 657 relates to a process for the manufacture of ketones where monocarboxylic acids having a boiling point exceeding 300° C. are heated in the liquid phase with small amounts of catalytically active metal compounds, silica gels or silicates to temperatures not substantially exceeding 300° C. The organic acid is mixed with the catalytically active species and subsequently heated to the desired reaction temperature. The process is reported to yield the desired ketones in good yield and purity. However, if the fatty acid starting material comprises fatty acids or fatty acid derivatives having a boiling point of less than 300° C. (which is the case for linear fatty acids having 12 carbon atoms or less such as lauric acid, capric acid, caprylic acid . . . ) in a more than insignificant amount, the process described in DE 295 657 does not lead to the desired ketones in good yields.

In EP2468708 document, cross-ketonization reactions are performed in non-aqueous solvent using magnetite nanopowders as catalyst to obtain arylalkylketone. However distillation under reduced pressure is required to separate the desired product from the high boiling solvent which can be costly at industrial scale. Furthermore, long reaction times (in their examples 21 h) are required to reach high yields.

It was thus a first object of the present invention to develop a facile and easy to use process for the synthesis of ketones by decarboxylative ketonization of fatty acids or fatty acid derivatives in a liquid phase.

Process P for Making Internal Ketones K1

Summarized Description of the Process P

This first object has been achieved by a process P for synthesizing an internal ketone K1 by decarboxylative ketonization reaction of a fatty acid, a fatty acid derivative or a mixture thereof in a liquid phase with a metal compound as catalyst in a reaction medium, said process P being characterized in that a ketone K2 at liquid state, which is identical or similar to the internal ketone K1, is introduced into the reaction medium.

Preferably, the metal compound is selected from iron oxides, such as FeO, $Fe_3O_4$ or $Fe_2O_3$.

According to an embodiment of the invention, water formed during the reaction is continuously removed from the reaction medium.

According to an embodiment, the reaction medium is substantially free of third solvents.

Preferably, during the reaction, the molar ratio of fatty acid, fatty acid derivative or mixture thereof to metal is in the range of from 6:1 to 99:1.

According to an embodiment, the ketone K2 is identical to internal ketone K1 and the ketone K2 introduced is originated from a previous process P for synthesizing an internal ketone K1 by decarboxylative ketonization reaction of a fatty acid, a fatty acid derivative or a mixture thereof.

According to an embodiment, the fatty acid, fatty acid derivative or mixture thereof comprises at least 10 mol %, based on the entire amount of fatty acid and fatty acid derivative, of fatty acid having 12 carbon atoms or less or derivative of fatty acid having 12 carbon atoms or less or mixture thereof.

According to an embodiment, a fatty acid derivative is used as starting material and is selected from esters and anhydrides.

According to an embodiment of the invention, one and only one fatty acid, such as capric acid or lauric acid, is used as starting material. According to another embodiment of the invention, a fatty acid cut is used as starting material.

Preferably, the reaction medium is maintained at a temperature ranging from 270° C. to 400° C., preferably until full conversion of the fatty acid or fatty acid derivative or mixture thereof and disappearance of optionally formed intermediate metallic salts.

According to an embodiment of the invention, the process P comprises the steps of:

a) introducing in any order at least part of the ketone K2 at liquid state, at least part of the metal compound, at least part of the fatty acid, fatty acid derivative or mixture thereof into a reactor in order to synthesize the internal ketone K1, said reactor optionally containing before said introduction, a part of the metal compound, and/or a part of the fatty acid, fatty acid derivative or mixture thereof and/or a part of the ketone K2 and/or a part of the internal ketone K1, b) recovering the internal ketone K1 optionally together with the ketone K2, and preferably together with the ketone K2, c) optionally recycling at least part of the internal ketone K1 and/or ketone K2 and/or at least part of the metal compound to step a).

Preferably, step a) comprises the steps:

a1) introducing at least part of the ketone K2 at liquid state, and at least part of the metal compound into a reactor, said reactor optionally containing before said introduction, a part of the metal compound, and/or a part of the fatty acid, fatty acid derivative or mixture thereof, and/or a part of the ketone K2 and/or a part of the internal ketone K1, a2) introducing at least part of the fatty acid, fatty acid derivative or mixture thereof into the reactor, optionally with:

a part of the metal compound, and/or a part of the ketone K2 and/or, a part of the intermediate metallic carboxylate salts obtained by reacting metal compound and the fatty acid or fatty acid derivative or mixture thereof before decomposition to form the internal ketone K1.

Preferably, at step a) of the process P of the invention, the fatty acid, fatty acid derivative or mixture thereof is introduced sequentially or continuously into the reactor.

According to an embodiment, during step a1), the reactor is substantially free of fatty acid and fatty acid derivative.

The process P of the present invention is easy to implement since it is performed in a liquid phase, and generally at ambient pressure.

The process P of the invention uses substoechiometric (catalytic) amount of metal compound and does not need the further use of a third solvent; the isolation of product ketones from reaction mixture is therefore easier.

The process P of the present invention provides ketones with a high yield and selectivity with a relatively short reaction time and high productivity.

The process P of the invention is well adapted to a continuous implementation.

Detailed Description of the Process P

The present invention is directed to a process P for synthesizing an ketone

K1 by decarboxylative ketonization reaction of a fatty acid, a fatty acid derivative or a mixture thereof in a liquid phase with a metal compound as catalyst in a reaction medium, said process P being characterized in that a ketone K2 at liquid state, which is identical or similar to the internal ketone K1, is introduced into the reaction medium.

Suitable metals for use in the process P in accordance with the present invention are selected from the group consisting of Mg, Ca, Al, Ga, In, Ge, Sn, Pb, As, Sb, Bi, Cd and transition metals having an atomic number of from 21 to 30. Suitable metal compounds are oxides of the aforementioned metals, carboxylate salts of the aforementioned metals, naphthenate salts of the aforementioned metals or acetate salts of the aforementioned metals, preferably metal compounds are oxides of the aforementioned metals. Magnesium, iron, and their oxides, are particularly preferred as metal compounds.

In accordance with a preferred embodiment the metal compound is iron(II) oxide or iron(III) oxide or a mixed oxide of iron(II) and iron (III) such as e.g. FeO, $Fe_3O_4$ or $Fe_2O_3$. Iron powder has economical advantages as it is cheap and abundantly available. It has been observed that iron oxides are efficient to promote the reaction reducing the overall reaction times.

According to the invention, the catalysis of the reaction may be qualified as a homogeneous catalysis since in the reaction conditions an intermediate metal carboxylate salt (i.e. iron carboxylate) is formed through the initial reaction between the fatty acid or its derivative with the metal compound and this intermediate salt is substantially soluble in the reaction medium.

The process P of the invention is characterized in that a ketone K2 at liquid state is introduced into a reactor.

The ketone K2 may be identical or similar to the internal ketone K1 to be synthetized.

The ketone K2 has usually a high boiling point of at least 170° C., advantageously of at least 220° C., preferably of at least 270° C., more preferably of at least 290° C. and even more preferably of at least 310° C. On the other hand, the boiling point of the ketone K2 is usually of at most 600° C., preferably of at most 500° C. and more preferably of at most 410° C. As herein used, the term "boiling point" generally denotes the normal boiling point (also called the atmospheric boiling point or the atmospheric pressure boiling point) of a liquid; it corresponds to the case in which the vapor pressure of the liquid equals the defined atmospheric pressure at sea level, 1 atmosphere. It can be measured by differential scanning calorimetry using for example a METTLER Toledo equipment.

By "a ketone K2 similar to the internal ketone K1", it is to be understood that the difference between the boiling point of the internal ketone K1 and the boiling point of the ketone K2 is equal to or lower than 80° C. Preferably, the difference between the boiling point of the internal ketone K1 and the boiling point of the ketone K2 is equal to or lower than 40° C., preferably equal to or lower than 10° C., more preferably equal to or lower than 5° C., even more preferably equal to or lower than 3° C.

Non limitative examples of ketones suitable as ketone K2 in accordance with the present invention are 5-nonanone (bp: about 186-187° C.), methyl levulinate (bp: about 193-195° C.), acetophenone (bp: about 202° C.), propiophenone (bp: about 218° C.), 6-undecanone (bp: about 228° C.), 7-tridecanone (bp: about 261° C.), 8-pentadecanone (bp: about 291° C.), benzophenone (bp: about 305° C.), 8-heptadecanone (predicted bp: about 309° C.), 8-octadecanone (predicted bp: about 323° C.), benzoin (bp: about 339-343° C.), 10-nonadecanone (predicted by: about 343° C.), anthraquinone (bp: about 379-381° C.), 12-tricosanone (predicted bp: about 387° C.), trans, trans dibenzylideneacetone (bp: about 401° C.), 13-pentacosanone (predicted by: about 410° C.), 14-heptacosanone (predicted bp: about 432° C.), 16-hentriacontanone (predicted bp: about 472° C.), 18-pentatriacontanone (bp: about 490° C.), 19-heptatriacontanone (predicted bp: about 523° C.) and 20-nonatriacontanone (predicted bp: about 532° C.).

The ketone K2 is advantageously an internal ketone. The ketone K2 is preferably one or more ketone(s) selected from internal ketones K1 susceptible of being synthesized by the process P, more preferably one or more ketone(s) selected from internal ketones K1 synthesized by the process P. Besides, the ketone K2 introduced into the reaction medium is advantageously one or more ketone(s) selected from ketones having from 7 to 35 carbon atoms, preferably from 15 to 35 carbon atoms, possibly from 19 to 35 carbon atoms. Finally, the ketone K2 introduced into the reaction medium is advantageously one or more ketone(s) selected from aliphatic ketones.

The ketone K2 may consist of one and only one ketone or may be a mixture of ketones. The ketone K2 may a single ketone or a mixture of ketones wherein the ketone(s) is/are susceptible of being obtained by decarboxylative ketonization reaction of a fatty acid, a fatty acid derivative or a mixture thereof. The ketone K2 may be one and only one ketone or a mixture of ketones wherein the ketone(s) has/have been obtained by decarboxylative ketonization reaction of a fatty acid, a fatty acid derivative or a mixture thereof.

When ketone K2 is a mixture of ketones, said mixture may be homogeneous (i.e. uniform in composition) or heterogeneous; it is preferably homogeneous. When ketone K2 is a mixture of ketones, the ketones of which the mixture is composed are generally at least partially miscible with each other; they are preferably fully miscible with each other. When ketone K2 is a mixture of ketones, said mixture of ketones has advantageously one and only one boiling point. In case of a mixture of ketones, the expression "boiling point of the ketone" is to be understood as the boiling point of the mixture of ketones when said mixture of ketones has one and only one boiling point and as the lowest boiling point of the mixture of ketones when said mixture of ketones has several boiling points.

Preferably, the ketone K2 is a mixture of ketones.

According to an embodiment, the ketone K2 introduced at step a) is originated from a previous process P for synthesizing a ketone by decarboxylative ketonization reaction of a fatty acid, a fatty acid derivative or a mixture thereof, said previous process P being preferably identical to the process P of the invention. In such an embodiment, wherein the fatty acid(s)/fatty acid derivatives(s) for producing the ketone K2 is identical to the fatty acid(s)/fatty acid(s) derivative(s) used in step b) of the process P of the invention, the ketone K2 will be very similar or identical to the internal ketone K1.

The terms "fatty acid" refer to a carboxylic acid containing at least 4 carbon atoms; besides, a fatty acid contains generally at most 28 carbon atoms. The terms "fatty acid derivative" refers to an anhydride made by the condensation of 2 fatty acids or to an ester made by the condensation of a fatty acid with an alcohol.

Suitable fatty acid derivatives are esters and anhydrides of fatty acids, but the use of the free fatty acids as such is generally preferred. The esters or anhydrides in the course of the reaction are converted to the acids which then react with the metal or the metal compound. Especially in case of esters, however, alcohols are formed as a by-product which then has to be removed at a later point in time, which requires additional step and costs. However, if esters are derived from lower alcohols such as for example methanol, ethanol, propanol or butanol, the alcohols may be removed progressively over the course of the reaction thanks to a reactive distillation.

The fatty acids or fatty acid derivatives can be used in the form of so called fatty acids or fatty acid derivatives cuts which may be obtained by the hydrolysis or alcoholysis of different natural fats and oils. Accordingly these cuts may contain various amounts of different linear fatty acids or linear fatty acid derivatives with different chain lengths. Just by way of examples, fatty acid cuts obtained from coconut oil and comprising mainly $C_{12}$-$C_{18}$ fatty acids may be mentioned here. The skilled person is well aware of other fatty acid cuts obtainable form various sources and will select the best suitable starting materials based on the desired ketones.

According to an embodiment of the invention, fatty acids having 12 carbon atoms or less, preferably of from 8 to 12 carbon atoms or derivatives of such acids (esters or anhydrides) constitute at least 10 mol % and preferably at least 15 mol % of the entire molar amount of a fatty acid mixture or fatty acid derivative mixture used as starting material. These acids lead to ketones having a total carbon number of 23 or less which have proved to be advantageous in a number of applications. There is no specific upper limit for the amount of these fatty acids or fatty acid derivatives of acids having 12 carbon atoms or less, i.e. the starting material may also entirely consist of such fatty acids and/or such fatty acid derivatives.

Subject to the above, preferred fatty acids for use in the process P of the present invention have at least 10 carbon atoms, such as hexanoic acid, isostearic acid, caprylic acid, capric acid, lauric acid, myristic acid, palmitic acid, stearic acid, arachidic acid, behenic acid, lignoceric acid, cerotic acid or mixtures thereof, and preferred fatty acid derivatives are the esters and anhydrides of these acids; more preferably, they have from 10 to 18 carbon atoms.

The fatty acids may be free of any —C═C— double bond of and of any —C≡O— triple bond. Non limitative examples of such fatty acids are the previously cited caprylic acid, capric acid, lauric acid, myristic acid, palmitic acid, stearic acid and mixtures thereof.

Alternatively, the fatty acids may comprise one or more double bonds and/or one or more triple bonds. Examples of fatty acids comprising one or more double bonds are oleic acid, linoleic acid, linolenic acid, erucic acid, palmitoleic acid, ricinoleic acid and mixtures thereof. Examples of fatty acids comprising one or more triple bonds are tariric acid, santalbic acid (which also comprises one double bond) and mixtures thereof.

When starting from a single fatty acid, a single symmetrical ketone is obtained as the reaction product; when starting from a cut of fatty acids as described above all the ketones formed by the combination of the different alkyl groups of the starting acids are obtained and the distribution of the different mixed ketones generally follows a statistical binomial law. The reaction equation can be summarized as follows:

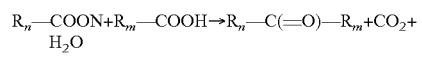

wherein $R_n$ and $R_m$ represent the aliphatic, e.g. alkyl, groups of the fatty acids present in the cut. It is well apparent that e.g. if three different acids are present, a total of six different ketones may be formed; three symmetrical ketones wherein $R_n$ and $R_m$ are identical and three mixed ketones with different groups $R_n$ and $R_m$.

The internal ketone K1 that is synthetized during the process P of the invention is an internal ketone.

According to an embodiment, the total amount of fatty acid material (fatty acid plus fatty acid derivative) added in the reaction medium for the decarboxylative ketonization reaction is such that the overall molar ratio of metal to carboxylic groups is in the range of from 1:6 to 1:99, i.e. the amount of metal is about 1 mol % to about 14 mol % and preferably of from 2 to about 10 mol % of the entire amount of fatty acid and fatty acid derivative.

For most of the processes described in the prior art in the liquid phase the metal or metal compound has been used in amounts of more than 50 mol % and in many cases even exceeding equimolar amounts. Such high amounts of metal are not necessary in the process P in accordance with the present invention which is a technical as well as an economical advantage of the process P in accordance with the present invention over the prior art.

During the decarboxylative ketonization reaction, the temperature of the reaction medium inside the reactor may be maintained at high temperature, for example the temperature inside the reactor may range from 270° C. to 400° C., preferably from 285° C. to 350° C., more preferably from 300 to 350° C. The reaction medium may be maintained at high temperature until full conversion of fatty acid and disappearance of the optionally formed intermediate metallic salts.

The process P of the present invention is preferably carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

During the process of the invention, a reaction medium comprising:
  at least part of a ketone K2,
  at least part of the metal compound, and
  at least part of the fatty acid, fatty acid derivative or mixture thereof,
  may be obtained.

According to a particular embodiment of the invention, the process comprises the steps of:
  introducing at least part of the ketone K2 at liquid state, at least part of the metal compound, at least part of the fatty acid, fatty acid derivative or mixture thereof into a reactor in order to synthesize the internal ketone K1, said reactor optionally containing, before said introduction, a part of the metal compound, a part of the fatty acid, fatty acid derivative or mixture thereof, a part of the ketone K2 and/or a part of the internal ketone K1,
  recovering the internal ketone K1 together with the ketone K2,
  optionally recycling at least part of the internal ketone K1 and ketone K2 and/or at least part of the metal compound to step a).

The reaction medium may be formed in the reactor by introducing the different compounds at step a) according to any introduction policy.

According to a preferred embodiment, the metal compound is not mixed with the fatty acid or fatty acid derivative or mixture thereof before introduction into the reactor, in order to avoid the formation of metallic salt outside the reaction medium.

According to an embodiment of the invention, the process P of the invention further comprises an additional step after step a) and before step b) of maintaining the temperature of the reactor at a high temperature, preferably at a temperature ranging from 270° C. to 400° C., more preferably from 285 to 350° C., even more preferably from 300 to 350° C., until full conversion of fatty acid and disappearance of the optionally formed intermediate metallic salts.

According to an embodiment, the step a) of the previous embodiment of the process P of the invention comprises the steps of:
  a1) introducing at least part of the ketone K2 at liquid state, and at least part of the metal compound into a reactor, said reactor optionally containing, before said introduction, a part of the metal compound, a part of the fatty acid, fatty acid derivative or mixture thereof, a part of the ketone K2 and/or a part of the internal ketone K1,
  a2) introducing at least part of the fatty acid, fatty acid derivative or mixture thereof into said reactor, optionally with
    a part of the metal compound and/or
    a part of the ketone K2 and/or
    a part of the intermediate metallic carboxylate salts obtained by reacting metal compound and fatty acid or fatty acid derivative or mixture thereof before decomposition to form the internal ketone K1.

According to an embodiment of the invention, all the ketone K2 may be introduced during step a1) and/or all the fatty acid or fatty acid derivative or mixture thereof may be introduced during step a2).

According to an embodiment wherein the fatty acid, fatty acid derivative or mixture thereof is mixed with the metal compound before introduction into the reaction medium, metallic carboxylate salts may be obtained by a reaction between metal compound and the fatty acid, fatty acid derivative or mixture thereof; said reaction can be carried out at a temperature lower than 270° C.

According to said embodiment, the ketone K2 and the metal compound introduced at step a1) may be introduced separately or together into the reactor. Indeed, the ketone K2 and the metal compound may be mixed outside the reactor, before their introduction into the reactor or the ketone K2 and the metal compound may be mixed into the reactor after their separate introduction into the reactor.

During step a1), at least part of the metal compound is also introduced into the reactor. According to an embodiment, the reactor initially comprises, before step a1), a part of the metal compound, for example, after implementation of step b) (recovery of the synthetized ketones), a part of the metal compound remains in the reactor. According to another embodiment, all of the metal compound is introduced into the reactor during step a1).

According to an embodiment of the invention, at step a1), the reactor is substantially free, in particular totally free, of fatty acid and fatty acid derivative. According to said embodiment, when the ketone K2 is introduced into the reactor, said reactor is substantially free of fatty acid and substantially free of fatty acid derivative.

During step a2), the fatty acid, fatty acid derivative or mixture thereof are introduced in the liquid state into the reactor containing the ketone K2 and the metal compound, for example through a funnel equipping the reactor. They may be added sequentially or continuously and they are profitably added at a rate avoiding the build-up of substantial amounts of free acid in the reaction system as well as significant temperature drop. The progress of the reaction and the conversion of the starting materials to the ketones K1 as final products may be conveniently monitored through appropriate methods like IR analysis.

During step a2), the fatty acid, fatty acid derivative or mixture thereof is generally added over a period of time which depends notably on the overall amount of acid or acid derivative used as well as the overall amount of metal compound present into the reactor.

Once the fatty acid derivative or fatty acid added in the process P of the invention has been converted, the desired internal ketone K1 can be easily recovered e.g. by distillation at reduced pressure. One can take also advantage of the ferromagnetic properties of the at least one metallic compound formed during the reaction (such as iron oxide(s)) to separate the metallic compound from the ketone by applying a magnetic field. Another way to separate the ketone from the metal compound is through a simple decantation or a simple filtration as the metallic compound is not soluble in the reaction mixture containing the ketone obtained as the reaction product. The skilled person is aware of representative techniques so that no further details need to be given here.

At step b), the internal ketone K1 and the ketone K2 may be recovered together or separately, but preferably together. Indeed, according to a preferred embodiment of the invention, the ketone K2 and the internal ketone K1 are not separated.

The entire process P can be advantageously carried out under inert gas atmosphere and suitable inert gases are e.g. nitrogen or argon, to name only two examples.

The process P can also be done in a continuous way where iron oxides are separated off from the reaction product in another/third separation zone and the residue constituted mainly of iron oxide can be recycled back into the reactor. It has been found, that up to four cycles are possible without a significant loss of catalytic activity of the metal or metal compound.

In another embodiment of the process P of the present invention, at the end of step a) the metallic compounds are separated from the products, e.g. using conventional techniques, and then are recycled for the conversion of another batch of fatty acid or fatty acid derivative or mixture thereof preferably comprising at least 10 mol %, based on the entire amount of fatty acid and fatty acid derivative, of fatty acid having 12 carbon atoms or less or derivative of such fatty acid or mixture thereof.

In a same way, part of the ketones recovered at step b) can be recycled in order to perform step a) of the process P.

The yield of the desired ketones after step a) normally exceeds 60%, more preferably 70% and can be as high as more than 90%.

According to an embodiment of the process P of the invention, the reaction medium in the reactor does not contain substantial amount of a third solvent. In a particularly preferred embodiment, no substantial amount of third solvent is added during the process P of the invention. For example, the reactor preferably comprises less than 5% by weight of third solvent(s), more preferably less than 3% by weight of third solvent(s), even more preferably less than 1% by weight of third solvent(s), based on the total weight of the reaction medium, ideally the reactor comprises no third solvent(s).

Within the meaning of the present invention, by the expression "third solvent", it is to be understood, a solvent different from the internal ketone K1, the ketone K2, the fatty acid or fatty acid derivative, the by-products that could be generated during the reaction.

Within the meaning of the present invention, the expression "reaction medium" refers to the medium, within the reactor, wherein the decarboxylative ketonization reaction takes place.

The reactor may be any kind of reactors that are conventionally used for the synthesis of ketones, in particular for the synthesis of ketones in liquid phase.

Within the meaning of the present invention, by "side reactions products", it is to be understood any product formed during the decarboxylative ketonization reaction different from ketones. Among side reaction products, mention may be made of hydrocarbons such as alkanes or alkenes.

The process P of the invention may be a continuous or a batch process.

Method M for Making End Products from Internal Ketones K1

Summarized Description of the Method M

Internal ketones are versatile starting materials for a wide variety of end products.

It was thus another object of the present invention to build up a more facile and easier to use method for the preparation of a wide variety of end products.

This other object was achieved by a method M for the preparation of a compound from an internal ketone K1, said method M comprising:

synthesizing the internal ketone K1 by the process P as above described, and causing the internal ketone K1 to react in accordance with a single or multiple chemical reaction scheme involving at least one reagent other than the internal ketone K1, wherein at least one product of the chemical reaction scheme is the end compound that is not further caused to be chemically converted into another compound.

Internal ketones K1 obtained by the process P can be seen as easily functionalizable hydrophobic platform molecules which typically possess chain lengths that are not widely available in the nature. Downstream chemistry of high industrial interest can be realized starting from key intermediate internal ketones K1, especially in order to design and develop new valuable compounds (such as ones possessing twin-tail & Gemini structures), with a particular interest for surfactants.

The chemical reaction scheme can be a single reaction scheme. A single reaction scheme is advantageously represented as follows:

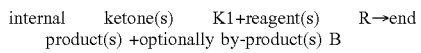

Alternatively, the chemical reaction scheme can be a multiple reaction scheme. A multiple reaction scheme is advantageously represented as follows:

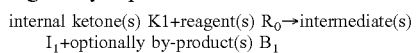

Optionally N further reaction(s) to convert intermediates into other intermediates:

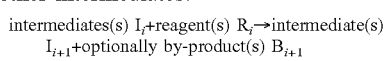

until final intermediate(s) $I_F$ is/are obtained, wherein N is a positive integer that can be equal to 0, 1, 2, 3, 4, 5 or higher, and $I_{N+1}=I_F$ intermediate(s) $I_F$+reagent(s) $R_F \rightarrow$end product(s)

Optionally, one or more of the above reactions is conducted in the presence of one or more catalyst(s). Irrespectively of whether a catalyst is present or not, reagent(s) R of above single reaction scheme and reagent(s) $R_0$ of the multiple reaction scheme are, for the purpose of the present invention, considered to react "directly" with the internal ketone K1.

As will be seen discussed thoroughly later on, possible reagents suitable for reacting directly with internal ketones K1 in a single or multiple chemical reaction scheme include ammonia, primary or secondary amines, mixtures of at least one aldehyde (including possibly formaldehyde) with ammonia or with at least one primary or secondary amine and alkylating agents.

Possible intermediates obtained by reacting internal ketones K1 directly with the aforementioned reagents include twin tail primary, secondary or tertiary amines, twin-tail tertiary amines themselves substituted by one or two primary, secondary or tertiary amino groups, internal ketone monoamines and internal ketone diamines such as amine Gemini compounds (typically with a central carbonyl group). All these intermediates can also be viewed as end products.

Possible end products obtained by further reacting the aforesaid intermediates with certain reagents include amphoteric compounds such as (poly)aminocarboxylates twin-tail amines, twin tail quaternary ammonium salts, internal ketone mono-quaternary ammonium salts, internal ketone di-quaternary ammonium salts such as quaternary ammonium salt Gemini compounds (typically with a central carbonyl group), aminoxide twin-tail amines, aminoxide Gemini compounds (typically with a central carbonyl group), dibetaine or disultaine twin-tail amines and betaine or sultaine Gemini compounds (typically with a central hydroxyl group). All these end products can also potentially serve as intermediates for forming still other end products.

Other particular reagents suitable for reacting directly with internal ketones ketones K1 in a single or multiple chemical reaction scheme include the diesters derived from tartaric acid, phenol and other aromatic mono- or polyalcohols, formaldehyde, pentareythritol, acrylates derivatives and hydrogen.

Possible end products obtained by reacting internal ketones K1 directly with the aformentioned particular other reagents and then, if needed, with ethylene and/or propylene oxide, include anionic surfactants such as dicarboxylate salt derivatives, non-ionic surfactants (especially non-ionic surfactants having a Gemini structure) and ethylenically unsaturated monomers.

DETAILED DESCRIPTION OF THE METHOD M

1—Making Amines from Internal Ketones K1
1.1) Reductive Amination to Afford Twin-Tail Amines
The end product can be a twin-tail amine.

Indeed, at least one internal ketone K1 (i.e. a single internal ketone or a mixture of internal ketones) that is advantageously synthesized by the process P can be reacted with at least one amine under reductive amination conditions to provide at least one twin-tail amine.

An internal ketone K1 synthesized by the process P is generally a compound of formula (I)

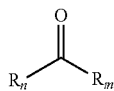

(I)

wherein $R_n$ and $R_m$ independently represent an aliphatic group, generally a $C_3$-$C_{27}$ aliphatic group, very often a $C_3$-$C_{19}$ aliphatic group, often a aliphatic $C_7$-$C_{17}$ group.

The number of carbon atoms of $R_n$ and $R_m$ can be even or odd numbers. They are advantageously odd numbers, which happens typically when the internal ketone K1 is made from a fatty acid containing an even number of carbon atoms (e.g. a $C_{23}$ internal ketone is made from a $C_{12}$ fatty acid).

For the reasons above explained when detailing the process P, $R_n$ and $R_m$ may be identical to each other; alternatively, $R_n$ and $R_m$ may differ from each other.

The number of carbon atoms of $R_n$ and of $R_m$, as herein represented by the couple (n,m), can be notably any of the following couples:

(3,3), (5,5), (7,7), (9,9), (11,11), (13,13), (15,15), (17,17), (19,19), (21,21), (23,23), (25,25), (27, 27)

(7,9), (7,11), (7,13), (7,15), (7,17), (7,19), (7,21), (7,23), (7,25), (7,27)

(9,11), (9,13), (9,15), (9,17), (9,19), (9,21), (9,23), (9,25), (9,27)

(11,13), (11,15), (11,17), (11,19), (11,21), (11,23), (11,25), (11,27)

(13,15), (13,17), (13,19), (13,21), (13,23), (13,25), (13,27)

(15,17), (15,19), (15,21), (15,23), (15,25), (15,27)

(17,19), (17,21), (17,23), (17,25), (17,27)

(19,21), (19,23), (19,25), (19,27)

(21,23), (21,25), (21,27)

(23,25), (23,27) or (25,27).

The aliphatic groups $R_n$ and $R_m$ may be linear or branched.

The aliphatic groups $R_n$ and $R_m$ may be free of any double bond and of any triple bond. Alternatively, the aliphatic groups $R_n$ and $R_m$ may comprise at least one —C=C— double bond and/or at least one —CH≡C— triple bond.

The aliphatic groups $R_n$ and $R_m$ are advantageously chosen from alkyl groups, alkenyl groups, alkanedienyl groups, alkanetrienyl groups and alkynyl groups.

Preferably, the aliphatic groups $R_n$ and $R_m$ are independently chosen from chosen from alkyl and alkenyl groups.

More preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often from $C_6$-$C_{17}$ alkyl and $C_6$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ alkyl group.

In particular, the at least one internal ketone K1 of formula (I) can be reacted with at least one amine of formula (II) under reductive amination conditions to afford the at least one twin-tail amine of formula (III)

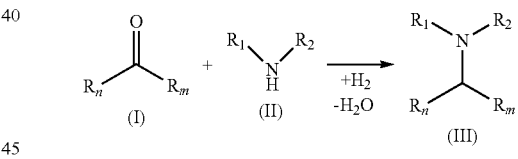

This amination reaction is preferably performed by reacting the ketone K1 of formula (I) and the amine of formula (II) in the presence of a transition metal (e.g. Ni, Co, Cu, Fe, Rh, Ru, Ir, Pd, Pt) based catalyst (typically Pd/C), in a autoclave under hydrogen pressure (typically from 1 atm to 200 bar).

According to a possible embodiment, the reaction is carried out in a solvent. However, the presence of such a solvent is not compulsory and according to a specific embodiment, no solvent is used for this step. The exact nature of the solvent, if any, may be determined by the skilled person. Typical suitable solvents include, without limitation, methanol, ethanol, isopropanol, tert-butanol, THF, 2-methyltetrahydrofuran, 1,4-dioxane, dimethoxyethane, diglyme and mixtures thereof.

Besides, this step is usually carried out at a temperature ranging from 15° C. to 400° C. and may be conducted batchwise, semi-continuously or continuously and generally performed either in a batch mode or in a continuous mode using a fixed-bed catalyst (gas-solid or gas-liquid-solid process).

In the above amine formula (II), $R_1$ and $R_2$ independently represent:

hydrogen or a linear or branched hydrocarbon radical having 1 to 24 carbon atoms which can be optionally substituted and/or interrupted by one or more heteroatoms or heteroatom containing groups (for example $R_1$ and $R_2$ can be selected from H, —$CH_3$, —$CH_2CH_3$, propyl, isopropyl, butyl, sec-butyl, isobutyl and tert-butyl), ethylamine of formula —$CH_2$—$CH_2$—NR'R" wherein R' and R" independently represent hydrogen or a short alkyl group having from 1 to 6 carbon atoms (such as for example $CH_3$, $CH_2CH_3$, propyl, isopropyl),

[poly(ethylenimine)]ethylamine of formula —(—$CH_2$—$CH_2$—NH—$)_m$—$CH_2$—$CH_2$—NR'R" wherein R' and R" independently represent hydrogen or an alkyl group having from 1 to 6 carbon atoms (such as for example $CH_3$, $CH_2CH_3$, propyl, isopropyl) and m is an integer from 1 to 20, hydroxyethyl of formula —$CH_2$—$CH_2$—OH,

[poly(ethylenimine)]ethanol of formula —(—$CH_2$—$CH_2$—NH—$)_m$—$CH_2$—$CH_2$—OH wherein m is an integer from 1 to 20, a N,N-dialkylaminoalkyl radical of formula —$(CH_2)_m$—NR'R" wherein m is an integer from 3 to 20 and R' and R" independently represent hydrogen or an alkyl group having 1 to 6 carbon atoms (such as $CH_3$, $CH_2CH_3$, propyl, isopropyl), and wherein $R_1$ and $R_2$ can also form an alkanediyl radical, typically of formula —$(CH_2)_m$— wherein m ranges from 3 to 8, which can be optionally interrupted or substituted by one or more heteroatoms or heteroatom containing groups; in this case, (II) is a cyclic amine such as pyrrolidine, piperidine, morpholine or piperazine.

As examples of amines (II), one can mention: ammonia, dimethylamine, monoethanolamine, diethanolamine, ethylenediamine (EN), diethylenetriamine (DETA), triethylenetetramine (TETA), tetraethylenepentamine (TEPA), aminoethylethanolamine (AEEA) and 3,3'-Iminobis(N,N-dimethylpropylamine).

1.2) Mannich Reaction Involving Condensation with an Aldehyde and an Amine to Afford Amine Gemini Compounds The end product can be an amine Gemini compound. Typically, the amine Gemini compound comprises a central carbonyl group which, in a two-dimensional representation of the formula of this compound, can form a symmetry axis provided some conditions are met on the nature of its substituents, as will immediately be made apparent from what follows.

Indeed, the at least one internal ketone K1 (i.e. a single internal ketone or a mixture of internal ketones) that is advantageously synthesized by the process P can be reacted with at least one aldehyde and at least one amine under Mannich reaction conditions to provide at least one ketone having one and only one of its carbonyl-adjacent carbon atoms substituted by an amine-containing group and/or at least one ketone having both of its carbonyl-adjacent carbon atoms substituted by an amine-containing group (Gemini amine).

In particular, internal ketones K1 of formula (I)

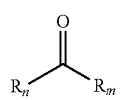

(I)

as above defined, wherein methylene groups are adjacent to the carbonyl group on its both sides can be represented by formula (I)'

(I')

wherein $R'_n$ and $R'_m$ independently represent an aliphatic group, generally a $C_2$-$C_{26}$ aliphatic group, very often a $C_2$-$C_{18}$ group, often a $C_5$-$C_{16}$ group.

The at least one internal ketone K1 of formula (I') can be reacted with at least one aldehyde of formula (IV) and at least one amine of formula (II) under Mannich reaction conditions to afford at least one ketone (Va) having one and only one of its carbonyl-adjacent carbon atoms substituted by an amine-containing group and/or at least one ketone (Vb) having both of its carbonyl-adjacent carbon atoms substituted by an amine-containing group (Gemine amine).

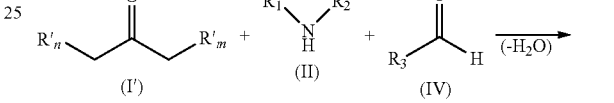

(Va)

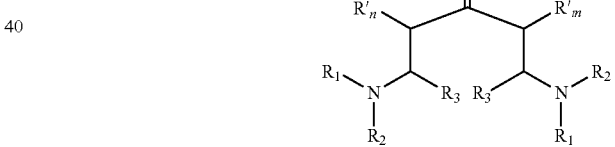

(Vb)

In the amine of formula (II), $R_1$ and $R_2$ are as previously defined in part 1.1

Regarding the aldehyde (IV), $R_3$ can represent:

hydrogen or a linear or branched hydrocarbon radical having from 1 to 24 carbon atoms which can be optionally substituted and/or interrupted by one or more heteroatoms or heteroatom containing groups (for example, $R_3$ can be selected from —H, —$CH_3$, —$CH_2CH_3$, propyl, isopropyl, butyl, sec-butyl, isobutyl and tert-butyl), or an aromatic or a heterocyclic aromatic radical which can be optionally substituted by one or more branched or linear hydrocarbon radical which can optionally contain one or more heteroatom (for example, $R_3$ can be phenyl, fur-2-yl, fur-3-yl, para-hydroxyphenyl, para-methoxyphenyl or 4-hydroxy-3-methoxyphenyl).

As examples of aldehydes (IV), one can mention formaldehyde, ethanal, propanal, butanal, furfural, hydroxymethylfurfural, vanillin and para-hydroxybenzaldehyde.

The amine Gemini compound (Vb) has a central carbonyl group. In a two-dimensional representation of formula (Vb), the central carbonyl group (C═O) can form a symmetry axis when substituents $R'_m$ and $R'_n$ are identical to each other.

The Mannich reaction can be conducted under acidic conditions when the amine (II) is in its protonated form, for example as a hydrochloride salt form.

The reaction is usually carried out by contacting the ketone K1 of formula (I'), the aldehyde (IV) and the amine (II) (or its protonated salt which can be generated in-situ by adding a stoichiometric amount of acid), optionally in the presence of an added solvent in a reaction zone at a temperature from 15° C. to 300° C. As examples of suitable solvents to conduct the reaction, one can mention: methanol, ethanol, isopropanol, toluene, xylenes, diglyme, dioxane, THF, methyl-THF, DMSO, etc.

The amine (II) or its protonated salt as well as the aldehyde (IV) can be used in molar excess and the excess reactants can be recovered at the end of the reaction and recycled.

The reaction can also be catalyzed by the addition of a suitable Bronsted or a Lewis acid. One can mention for example: $H_2SO_4$, HCl, triflic acid, p-toluenesulfonic acid, perchloric acid, $AlCl_3$, $BF_3$, metal triflate compounds such as aluminium triflate, bismuth triflate, heterogeneous solid acids such as Amberlyst resins, zeolithes, etc.

The water generated during the reaction can be optionally trapped thanks to a Dean-Stark apparatus.

If the reaction is conducted under acidic conditions, after subsequent work-up, the products (Va) and/or (Vb) are obtained in the form of their protonated salts which can be neutralized in a second stage by the reaction with an aqueous solution of a suitable base for example: NaOH, KOH, $NH_4OH$, $Na_2CO_3$.

The desired ketones (Va) and/or (Vb) are obtained after appropriate work-up. The skilled person is aware of representative techniques so that no further details need to be given here.

2—Making from Internal Ketones K1

2.1) Quatemization of Twin-Tail Tertiary Amines to Afford Twin-Tail Quaternary Ammonium Compounds The end product can be a twin-tail quaternary ammonium compound.

Such a twin-tail quaternary ammonium compound can be obtained as end product when at least one twin-tail amine obtained from the at least one internal ketone K1 according to the reaction described in part 1.1 is a teriary amine. For example, when the twin-tail amine is of formula (III), this happens when $R_1$ and $R_2$ differ from a hydrogen atom.

Accordingly, at least one twin-tail tertiary amine obtained from at least one internal ketone K1 according to the reaction described in part 1.1 can be reacted with at least one alkylating agent to obtain at least one twin-tail quaternary ammonium salt.

In particular, at least one tertiary amine (III) obtained from the at least one internal ketone K1 of formula (I) according to part 1.1 can be reacted with at least one alkylating agent (VI) of formula $R_4$-X to obtain at least one twin-tail quaternary ammonium salt (VII), as schemed below:

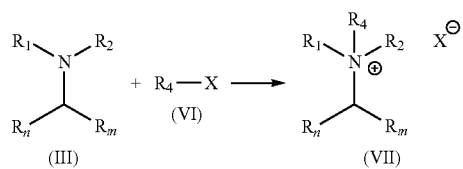

As already pointed out, amines (III) useful for use in present part 2.1 are tertiary amines. Advantageously, the tertiary amines (III) useful for use in present part 2.1 are tertiary amines wherein $R_1$ and $R_2$ independently represent a linear or branched hydrocarbon radical having from 1 to 24 carbon atoms which can be optionally substituted and/or interrupted by one or more heteroatoms or heteroatom containing groups (for example $R_1$ and $R_2$ can be selected from —$CH_3$, —$CH_2CH_3$, propyl, isopropyl, butyl, sec-butyl, isobutyl and tert-butyl) and tertiary amines wherein $R_1$ and $R_2$ form an alkanediyl radical, typically of formula —$(CH_2)_m$— wherein m ranges from 3 to 8, which can be optionally interrupted and/or substituted by one or more heteroatoms or heteroatom containing groups.

The group X contained in the alkylating agent (VI) and that constitutes the counter anion of the salt (VII) is a leaving group, typically a halide such as Cl, Br or I, methylsulfate (—$SO_4Me$), sulfate (—$SO_4$), a sulfonate derivative such as methanesulfonate (—$O_3S$—$CH_3$), para-toluenesulfonate (—$O_3S$—$C_7H_7$) or trifluoromethanesulfonate (—$O_3S$—$CF_3$).

In reactant (VI), $R_4$ represents a linear or branched hydrocarbon radical having 1 to 10 carbon atoms which can be optionally substituted and/or interrupted by a substituted or unsubstituted aromatic group and/or a heteroatom or heteroatom containing group. For example, R4 can be: —$CH_3$, —$CH_2CH_3$, benzyl, furfuryl.

As examples of alkylating agent (VI), one can mention dimethyl sulfate, methyl chloride, methyl bromide, methyl triflate, benzyl chloride and epichlorhydrin.

This reaction can be carried out by contacting both reactants in a reaction zone at a temperature from 15° C. to 400° C., optionally in the presence of an added solvent such as methanol, ethanol, isopropanol, toluene, a xylene, diglyme, dioxane, THF, methyl-THF or DMSO. The alkylating agent can be used in stoichiometric amounts or in excess and the excess reactant can be recovered after the reaction following a suitable work-up and recycled. The skilled person is aware of representative work-up techniques so that no further details need to be given here.

2.2) Quatemization Reaction of Tertiary Amine Gemini Compounds to Afford Quaternary Ammonium salt Gemini Compounds The end compound can be a quaternary ammonium salt Gemini compound. Typically, the quaternary ammonium salt Gemini compound comprises a central carbonyl group which, in a two-dimensional representation of the formula of this compound, can form a symmetry axis provided some conditions are met on the nature of its substituents, as will immediately be made apparent from what follows.

Such a quaternary ammonium salt Gemini compound can be obtained as end product when at least one tertiary amine Gemini compound obtained from at least one internal ketone K1 according to the reaction described in part 1.2 is a tertiary amine Gemini compound. For example, when the amine Gemini compound is of formula (Vb), this happens when $R_1$ and $R_2$ differ from a hydrogen atom.

At least one tertiary amine Gemini compound obtained from at least one internal ketone K1 according to the reaction described in part 1.2 can be reacted with at least one alkylating agent to obtain at least one quaternary ammonium salt Gemini compound.

For example, at least one ketone (Va) and/or at least one ketone (Vb) obtained from the at least one internal ketone K1 of formula (I) according to part 1.2 can be reacted with at least one alkylating agent (VI) of formula $R_4$-X to obtain respectively at least one quaternary ammonium salt (VIIIa)

and/or at least one quaternary ammonium salt Gemini compound (VIIIb), as schemed below:

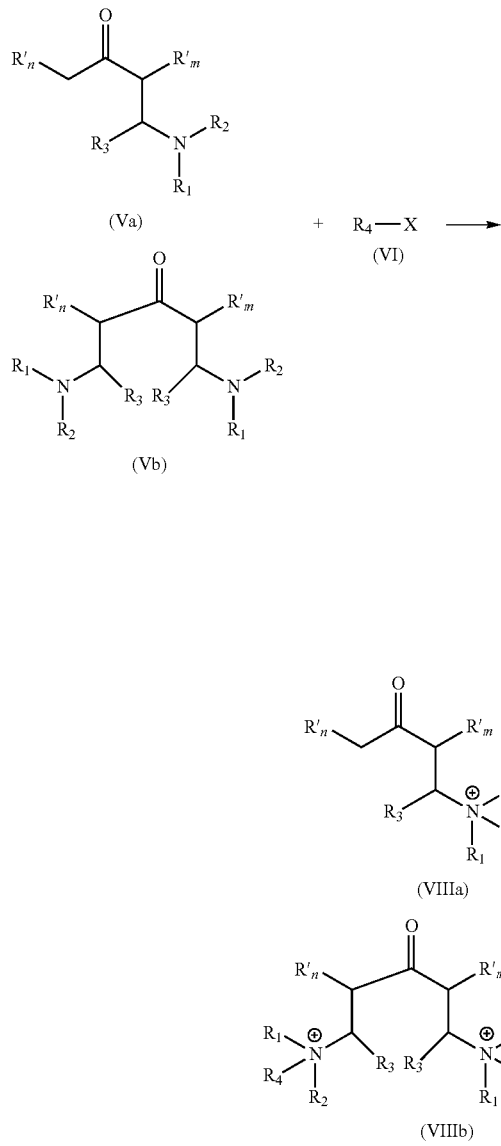

(Va)

+ R$_4$—X (VI) →

(Vb)

(VIIIa)

(VIIIb)

The substituents R$_1$, R$_2$, R$_4$ and the group X meet the same definitions as the ones provided in part 2.1 while the substituent R$_3$ has the same definition as in part 1.2.

This reaction can be carried out as indicated in part 2.1.

3—Making Amphoterics from Internal Ketones K1

The end compound can be a twin-tail (poly)aminocarboxylate.

3.1) First Synthesis of Twin-Tail (poly)aminocarboxylates

At least one twin-tail tertiary amine prepared from at least one internal ketone K1 according to part 1.1 can be reacted with at least one alkylating agent to afford at least one amphoteric compound, notably when said twin-tail tertiary amine is itself substituted by at least one, possibly by two and only two, amino groups (—NH$_2$).

Certain amines of formula (III) that are suitable for undergoing this reaction comply with formula (III')

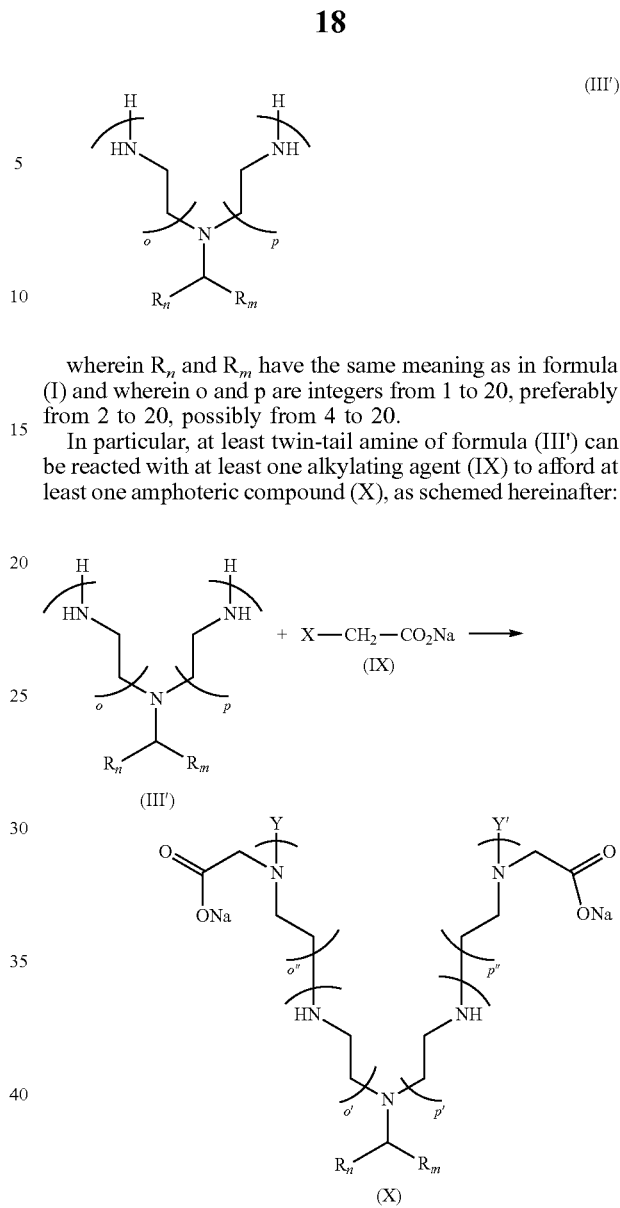

(III')

wherein R$_n$ and R$_m$ have the same meaning as in formula (I) and wherein o and p are integers from 1 to 20, preferably from 2 to 20, possibly from 4 to 20.

In particular, at least twin-tail amine of formula (III') can be reacted with at least one alkylating agent (IX) to afford at least one amphoteric compound (X), as schemed hereinafter:

(III') + X—CH$_2$—CO$_2$Na (IX) →

(X)

The reaction is usually conducted by contacting both reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 to 9.5. This adjustment can be done by adding required amounts of concentrated NaOH and/or HCl aqueous solutions to the reaction medium.

Importantly, by adjusting the stoichiometry of the reaction (molar excess of (IX) with respect to (III')), it is possible to adjust the average degree of alkylation of the starting amine (III') which means the average number of methylenecarboxylate groups (—CH$_2$—CO$_2$Na) contained in (X).

In the product (X), o', o", p' and p" are integers ranging from 0 to 20 provided that at least one of o" and p" is of at least 1. Preferably, o', o", p' and p" are integers ranging from 1 to 20, possibly from 2 to 20, and the following equalities must be respected:

o'+o"=o and p'+p"=p.

The substituents Y and Y' can be independently a hydrogen atom or a methylenecarboxylate fragment (—CH$_2$—CO$_2$Na).

It has to be understood that the values of o', o", p' and p" reflect the degree of alkylation and that mixture of compounds (X) with different values for o', o", p' and p" and with different substituents Y and Y' can be obtained. Globally, one can say that when the molar amount of the alkylating agent (IX) is increased, the value of o" and p" increase (and consequently o' and p' decrease).

The group X contained in the alkylating agent (IX) is a leaving group, and has the same meaning as in part 2.1.

As an example, one can consider the reaction between the ethylenediamine-derived amine of type (III') and 2 equivalents of sodium monochloroacetate ((IX) with X=Cl). In this case, the following mixture can be obtained:

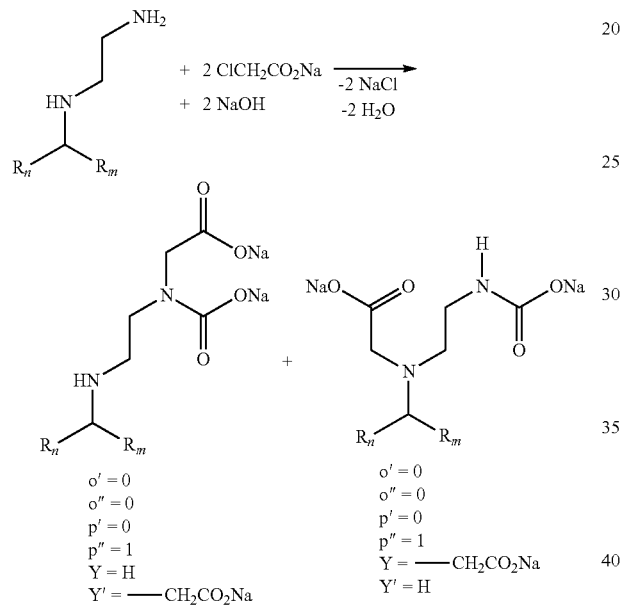

3.2) Second Synthesis of (poly)aminocarboxylates

At least one twin-tail tertiary amine prepared from at least one internal ketone K1 according to part 1.1 can be reacted with at least one acrylate derivative (especially a hydrocarbyl acrylate of formula CH$_2$=CH—CO$_2$A wherein A is hydrocarbyl, preferably C$_1$-C$_7$ hydrocarbyl, more preferably C$_1$-C$_4$ alkyl), to afford at least one amphoteric compound, notably when said twin-tail tertiary amine is itself substituted by at least one, possibly by two and only two, amino groups (—NH$_2$).

Certain amines of formula (III) that are suitable for undergoing this reaction comply with formula (III') as described in part 3.1.

In particular, the at least one twin-tail amine (III') obtained from the at least one internal ketone K1 (I) according to part 1.1, wherein R$_n$ and R$_m$ have the same meaning as in formula (III) and wherein o and p are integers from 1 to 20, preferably from 2 to 20, possibly from 4 to 20, is reacted in a first step with at least one acrylate derivative, such as the above described hydrocarbyl acrylate, to undergo conjugate additions affording at least one ester, such as the hydrocarbyl ester of the formula (XIa')—not represented—obtained by generalizing/replacing methyl (Me) by hydrocarbyl (A substituent) in below formula (XIa). The at least one obtained ester (XIa') is then saponified in a second stage using an aqueous NaOH solution to afford at least one amphoteric compound, such as the amphoteric compound of formula (XIb')—not represented—again obtained by generalizing/replacing methyl (Me) by hydrocarbyl (A substituent) in below formula (XIb).

The following reaction scheme corresponds to the case when the acrylate derivative is CH$_2$=CH—CO$_2$Me (A is methyl Me):

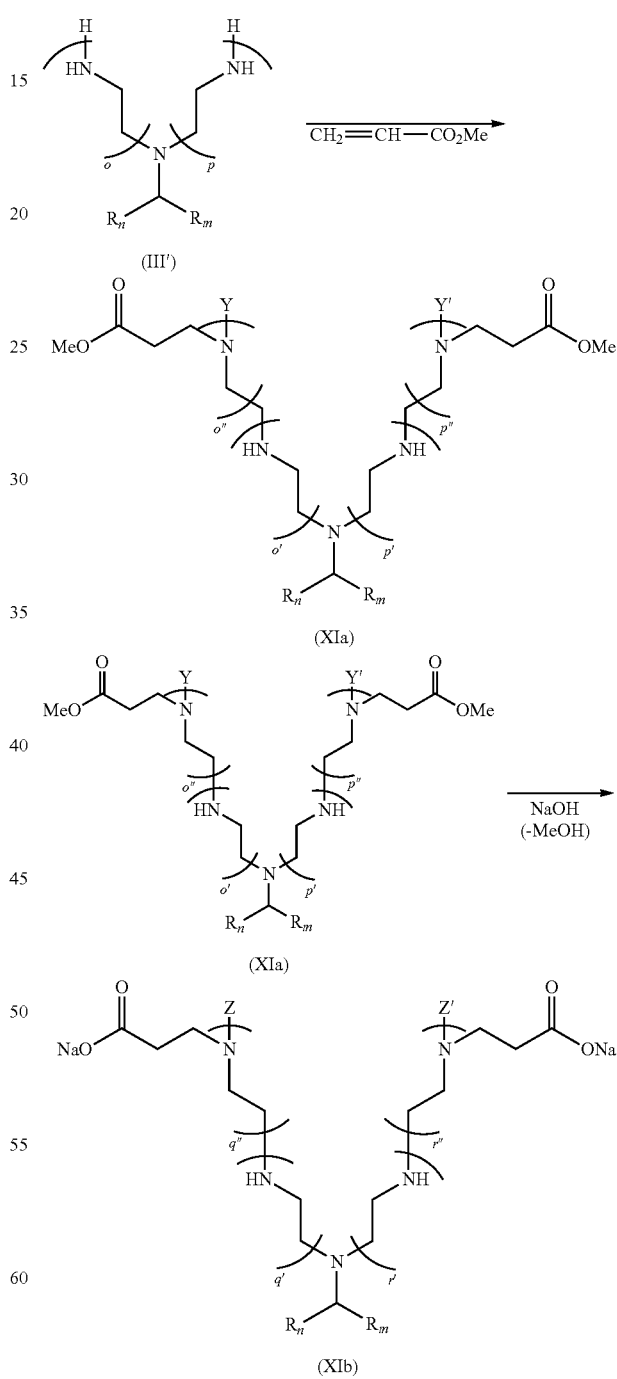

Typically, in the intermediate (XIa') [e.g. (XIa)], the substituents Y and Y' represent independently either a hydrogen atom or a hydrocarbyl ethylenecarboxylate fragment (—CH$_2$—CH$_2$—CO$_2$A), in particular a methyl ethylenecarboxylate fragment (—CH$_2$—CH$_2$—CO$_2$Me).

In the final amphoteric derivative (XIb') [e.g. (XIb)], the substituents Z and Z' independently represent a hydrogen atom or an ethylenecarboxylate fragment (—CH$_2$—CH$_2$—CO$_2$Na).

o', o", p' and p" in the intermediate (XIa') [e.g. (XIa)], and q', q", r' and r" in the final product (XIb') [e.g. (XIb)] are integers ranging from 0 to 20 provided that at least one of o" and p" is of at least 1 and at least one of q" and r" is of at least 1.

Preferably, o', o", p' and p" in the intermediate (XIa') [e.g. (XIa)], and q', q", r' and r" in the final product (XIb') [e.g. (XIb)] are integers ranging from 1 to 20, possibly from 2 to 20.

In addition, the following equalities must be respected:

o'+o"=q'+q"=o

'+p"=r'+r"=p

The first step of the reaction is carried out by contacting both reactants in a reaction zone at temperature from 15° C. to 400° C. The whole amount of the reactants can be introduced directly in the reaction mixture, but in a preferred embodiment the acrylate derivative is progressively added into the reaction mixture in order to limit polymerization side reactions. The reaction can be optionally conducted in the presence of an added solvent, for example: methanol, ethanol, isopropanol, THF, dioxane, ethyl acetate, acetonitrile, etc.

The acrylate derivative can be used in excess with respect of the amine (III').

The intermediate ester (XIa') [e.g. methyl ester (XIa)] is advantageously isolated after removal of excess of acrylate derivative and optional solvents using standard techniques well known by the skilled person of the art. The second step is then carried out by contacting intermediate (XIa') with an appropriate amount of an aqueous solution of NaOH (the molar amount of NaOH is equal or higher than the molar amount of ester fragments that need to be saponified), optionally in the presence of an added solvent, such as methanol, ethanol, isopropanol, acetonitrile, DMSO or THF, and at a temperature from 15° C. to 400° C.

During the first step, the acrylate derivative can be used in a molar excess, and generally the stoichiometric ratio between amine (III') and acrylate will dictate the average degree of alkylation of the starting amine (III'), meaning the average number of hydrocarbyl ethylenecarboxylate (—CH$_2$—CH$_2$—CO$_2$A) fragments contained in the intermediate (XIa') or the like and consequently the average number of ethylenecarboxylate (—CH$_2$—CH$_2$—CO$_2$Na) fragments contained in the final amphoteric product (XIb').

It has to be understood that when the molar excess of acrylate derivative is increased during the first step, the average number of hydrocarbyl ethylenecarboxylate (—CH$_2$—CH$_2$—CO$_2$A) fragments contained in the intermediate (XIa') and the average number of ethylenecarboxylate (—CH$_2$—CH$_2$—CO$_2$Na) fragments contained in the final amphoteric product (XIb') are increased.

Usually, a mixture of intermediates (XIa') [e.g. (XIa)] with different values for o', o", p', p" and different substituents Y and Y' is obtained at the end of the first step.

Same applies for the final products (XIb') [e.g. (XIb)] where mixtures of derivatives with different values for q', q", r', r" and different substituents Z and Z' are obtained at the end of the second step.

As an example, one can consider the reaction between the ethylenediamine-derived amine of type (III') and 2.5 equivalents of methyl acrylate followed by hydrolysis.

In this case the following mixture can be obtained:

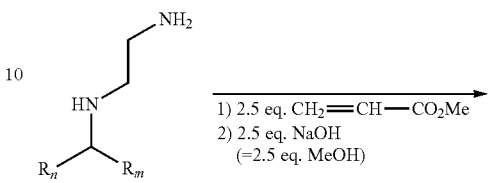

1) 2.5 eq. CH$_2$=CH—CO$_2$Me
2) 2.5 eq. NaOH
(=2.5 eq. MeOH)

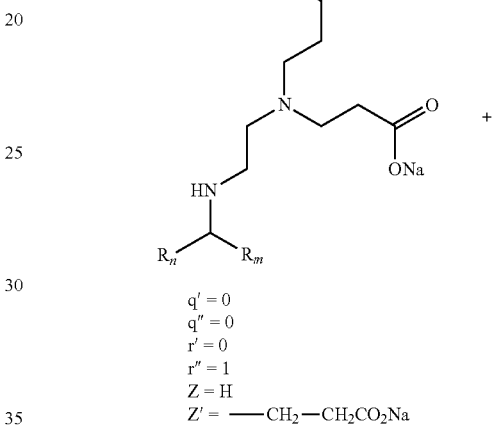

q' = 0
q" = 0
r' = 0
r" = 1
Z = H
Z' = —CH$_2$—CH$_2$CO$_2$Na

+

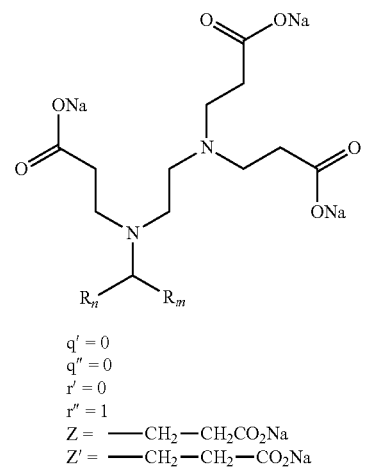

q' = 0
q" = 0
r' = 0
r" = 1
Z = —CH$_2$—CH$_2$CO$_2$Na
Z' = —CH$_2$—CH$_2$—CO$_2$Na 3.3) Third Synthesis of (poly)aminocarboxylates The reaction is conducted as described in part 3.1, except that the at least one starting amine (III) made from the at least one internal ketone K1 (I) is an amine (III") which contains one or two terminal 2-hydroxyethyl fragment(s) (—CH$_2$—CH$_2$—OH) based on the nature of Y.

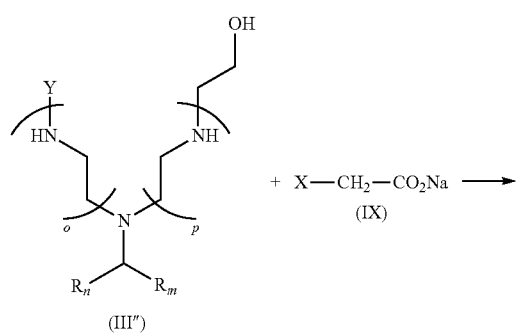

(III''')

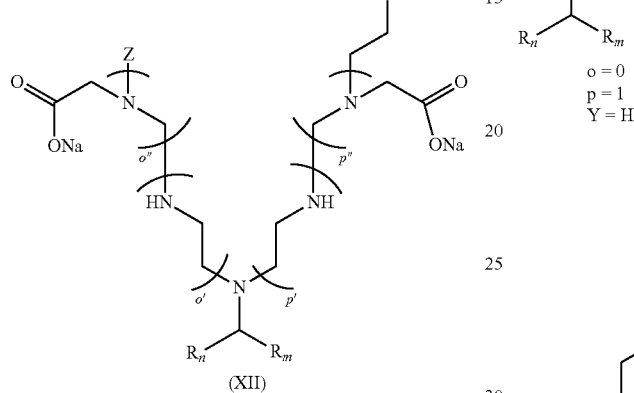

(XII)

Z = ——H or ——CH₂CO₂Na if Y = ——H
Z = ——CH₂CH₂OH or
——CH₂CH₂—O——CH₂CO₂Na if
Y = ——CH₂CH₂OH

What has been said in part 3.1 regarding the degree of alkylation applies in this case as well.

In the reaction scheme above:

o and p in the reactant (III''') are integers from 1 to 20, preferably from 2 to 20, possibly from 4 to 20;

o', o'', p' and p'' in the product (XII) are integers ranging from 0 to 20, provided at least one of o'' and p'' is of at least 1; preferably, o', o'', p' and p'' in the product (XII) are integers ranging from 1 to 20, possibly from 2 to 20, and the following equalities must be respected:

o'+o''=o p'+p''=p.

The substituent Y in the reactant (III''') represents a hydrogen atom or a 2-hydroxyethyl fragment (—CH₂—CH₂—OH).

The substituent Z contained in the product (XII) represents:
 hydrogen or methylenecarboxylate (—CH₂—CO₂Na) when Y is hydrogen,
 2-hydroxyethyl (—CH₂—CH₂—OH) or the ether fragment —CH₂—CH₂—O—CH₂—CO₂Na when Y is 2-hydroxyethyl fragment (—CH₂—CH₂—OH).

The substituent Z' represents hydrogen or methylenecarboxylate fragment —CH₂—CO₂Na.

As described in part 3.1, a mixture of products (XII) containing different numbers of methylenecarboxylate fragments (—CH₂—CO₂Na), which means different values for o', o'', p' and p'' and different substituents Z and Z', can be obtained.

As an example, one can consider the reaction between the aminoethylethanolamine-derived amine of type (III''') and 1.5 equivalents of sodium monochloroacetate [(IX) with X=Cl]. In this case, the following mixture can be obtained:

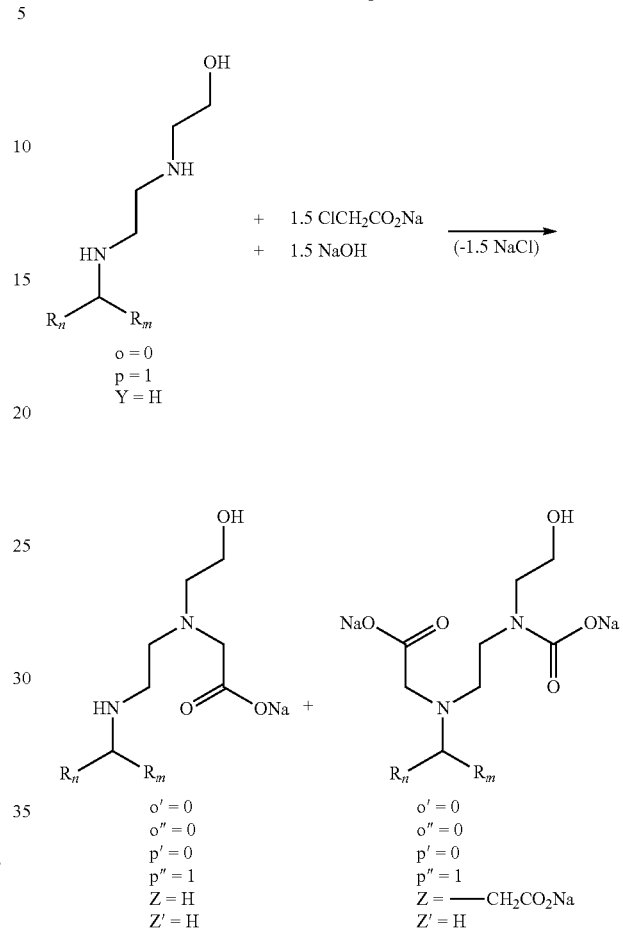

3.4) Fourth Synthesis of (poly)aminocarboxylates

The reaction is conducted as described in part 3.2, except that the at least one starting amine (III) made from the at least one internal ketone K1 (I) is an amine (III'') which contains one or two terminal 2-hydroxyethyl fragment(s) (—CH₂—CH₂—OH) based on the nature of Y.

An exemplary reaction scheme is:

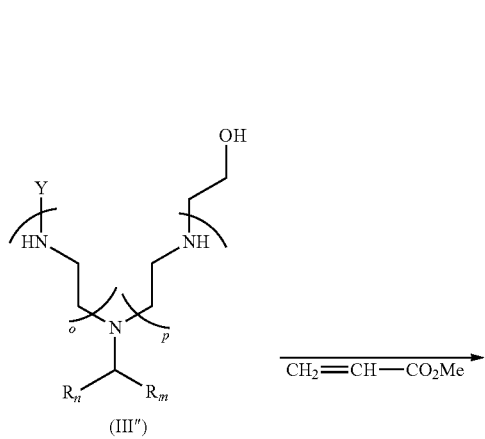

(III'')

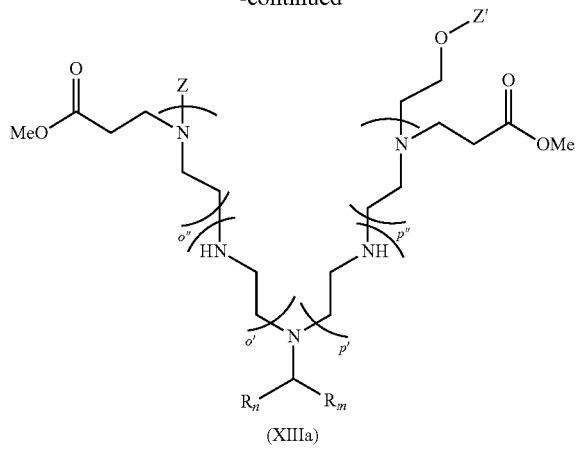

(XIIIa)
Z = H or CH$_2$CH$_2$CO$_2$Me if Y = H
Z = CH$_2$CH$_2$OH or
CH$_2$CH$_2$OCH$_2$CH$_2$CO$_2$Me if Y = CH$_2$CH$_2$OH
Z' = H or CH$_2$CH$_2$CO$_2$Me

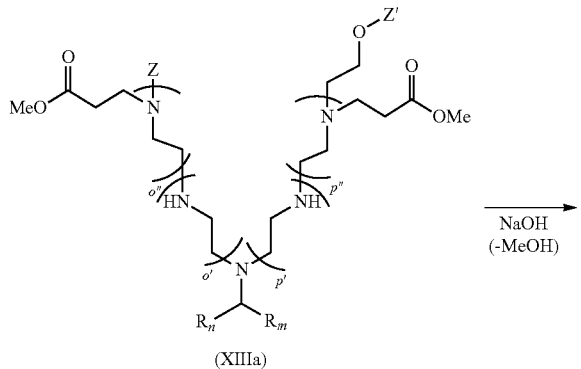

(XIIIa)

NaOH
(-MeOH)

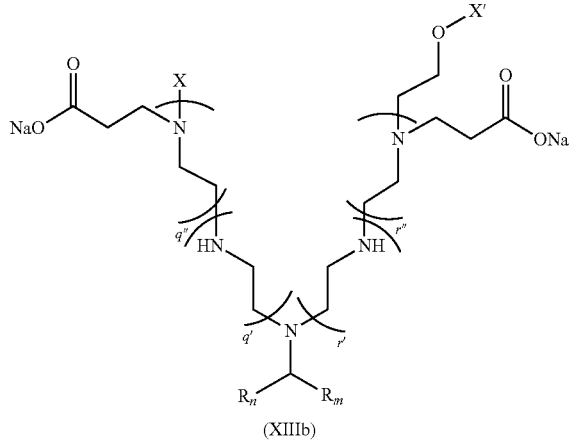

(XIIIb)
X = H or CH$_2$CH$_2$CO$_2$Na if Y = H
X = CH$_2$CH$_2$OH or
CH$_2$CH$_2$OCH$_2$CH$_2$CO$_2$Na if Y = CH$_2$CH$_2$OH
X' = H or CH$_2$CH$_2$CO$_2$Na

As in part 3.2, this exemplary reaction scheme can be generalized by replacing CH$_2$=CH—CO$_2$Me acrylate by hydrocarbyl acrylate of formula CH$_2$=CH—CO$_2$A, wherein A is as defined in part 3.2, and more generally by whatever acrylate derivative.

The substituent Y in the reactant (III″) represents a hydrogen atom or a 2-hydroxyethyl fragment (—CH$_2$—CH$_2$—OH).

In the above reaction scheme:
o and p in the reactant (III″) are integers from 1 to 20, preferably from 2 to 20, possibly from 4 to 20;
o', o″, p' and p″ in the intermediate (XIIIa) [or in its non-represented generalization (XIIIa') wherein Me is replaced by substituent A] and q', q″, r' and r″ in the final product (XIIIb) [or in its non-represented generalization (XIIIb') wherein Me is replaced by substituent A] are integers ranging from 0 to 20 provided that at least one of o″ and p″ is of at least 1 and at least one of q″ and r″ is of at least 1.

Preferably, o', o″, p' and p″ in the intermediate (XIIIa) or (XIIIa'), and q', q″, r' and r″ in the final product (XIIIb) or (XIIIb') are integers ranging from 1 to 20, possibly from 2 to 20.

In addition, the following equalities must be respected:

$$o'+o''=q'+q''=o$$

and $$p'+p''=r'+r''=p$$

The substituent Z in the intermediate (XIIIa') represents:
hydrogen or hydrocarbyl ethylenecarboxylate (—CH$_2$—CH$_2$—CO$_2$A) when Y is hydrogen,
2-hydroxyethyl fragment (—CH$_2$—CH$_2$—OH) or the ether fragment —CH$_2$—CH$_2$—O—CH$_2$—CH$_2$—CO$_2$A when Y is —CH$_2$CH$_2$OH.

The substituent Z' in the intermediate (XIIIa') represents either hydrogen or hydrocarbyl ethylenecarboxylate (—CH$_2$—CH$_2$—CO$_2$A). Thus, for example, when (XIIIa') is (XIIIa), Z' represents either hydrogen or methyl ethylenecarboxylate (—CH$_2$—CH$_2$—CO$_2$Me)

The substituent X in the end compound (XIIIb') [e.g. in the end compound (XIIIb)] represents:
hydrogen or ethylenecarboxylate (—CH$_2$—CH$_2$—CO$_2$Na) if Y is hydrogen
2-hydroxyethyl fragment (—CH$_2$—CH$_2$—OH), or the ether fragment —CH$_2$—CH$_2$—O—CH$_2$—CH$_2$—CO$_2$Na if Y is —CH$_2$CH$_2$OH, while the substituent X' in the end compound (XIIIb') represents either hydrogen or ethylenecarboxylate (—CH$_2$—CH$_2$—CO$_2$Na).

What has been said in part 3.2 regarding the impact on the alkylation degree of the molar ratio between the acrylate derivative and the substrate (III″) used in the first reaction step applies here as well.

As described in part 3.2, a mixture of intermediates (XIIIa') [e.g. (XIIIa)] and a mixture of end products (XIIIb') [e.g. (XIIIb)] are usually obtained.

4—Aminoxides 4.1) Synthesis of aminoxide Twin-Tail Amines

The end compound can be an aminoxide twin-tail amine, that is to say a twin-tail amine substituted by at least one aminoxide moiety. The aminoxide twin-tail amine can be substituted by one and only one or two and only two moiety(-ies).

At least one aminoxide twin-tail amine can be obtained from at least one twin-tail tert-amino amine (that is to say an amine that is itself substituted by at least one tert-amino group), which is itself previously obtained from at least one internal ketone K1.

To this effect, a certain twin-tail amine of formula (III) obtained from at least one internal ketone K1 of formula (I) is advantageously used as reagent, namely a twin-tail tert-amino amine of formula (III$^{3'}$):

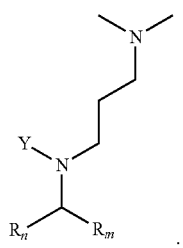
(III³')

The following reaction scheme can be followed:

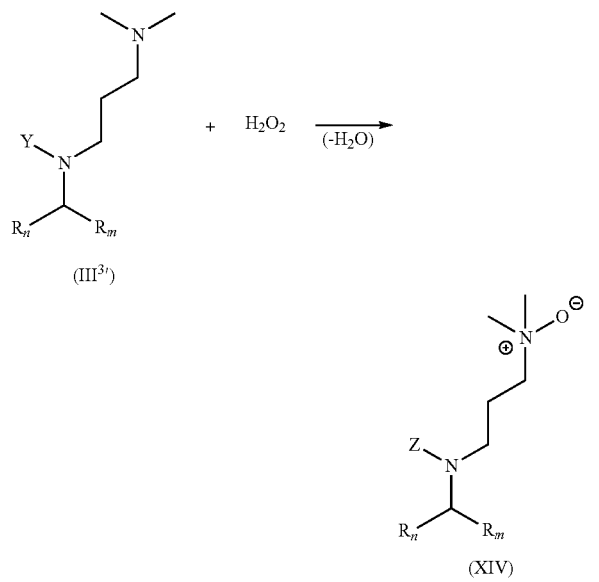

In the above scheme, Y is either hydrogen or 3-dimethylaminopropyl fragment (—$CH_2$—$CH_2$—$CH_2$—$N(CH_3)_2$); Z is hydrogen when Y is hydrogen and Z is the 3-dimethylaminoxide propyl fragment (—$CH_2$—$CH_2$—$CH_2$—N($CH_3)_2$O) when Y is 3-dimethylaminopropyl fragment (—$CH_2CH_2CH_2$—$N(CH_3)_2$).

This reaction can be conducted by contacting the twin-tail tert-amino amine (III³') obtained from the internal ketone K1 (I) with $H_2O_2$ (which can be used dissolved in aqueous solution) in a reaction zone at a temperature ranging from 15° C. to 400° C. and optionally in the presence of an added solvent. As examples of suitable solvents, one can mention methanol, ethanol, isopropanol, DMSO, acetonitrile, water, THF, dioxane or a mixture thereof.

In a preferred embodiment, $H_2O_2$ solution is progressively added into the reaction medium and can be used in molar excess with respect of the twin-tail tert-amino amine (III³'). The excess of $H_2O_2$ can be decomposed at the end of the reaction using appropriate techniques well known by the skilled person of the art.

4.2) Synthesis of aminoxide Gemini Compounds

The end product can be an aminoxide Gemini compound. Typically, the aminoxide Gemini compound comprises a central hydroxyl group which, in a two-dimensional representation of the formula of this compound, can form a symmetry axis provided some conditions are met on the nature of its substituents, as will immediately be made apparent from what follows.

In particular, at least one aminoxide Gemini compound of formula (XVIb) can be obtained from at least one internal ketone K1 of formula (I) using the ketone of formula (Vb) as intermediates.

It goes without saying that at least one aminoxide derivative of formula (XVIa) can likewise be obtained from at least one internal ketone K1 of formula (I) using the ketone of formula (Va) as intermediate.

A suitable reaction scheme is described hereinafter:

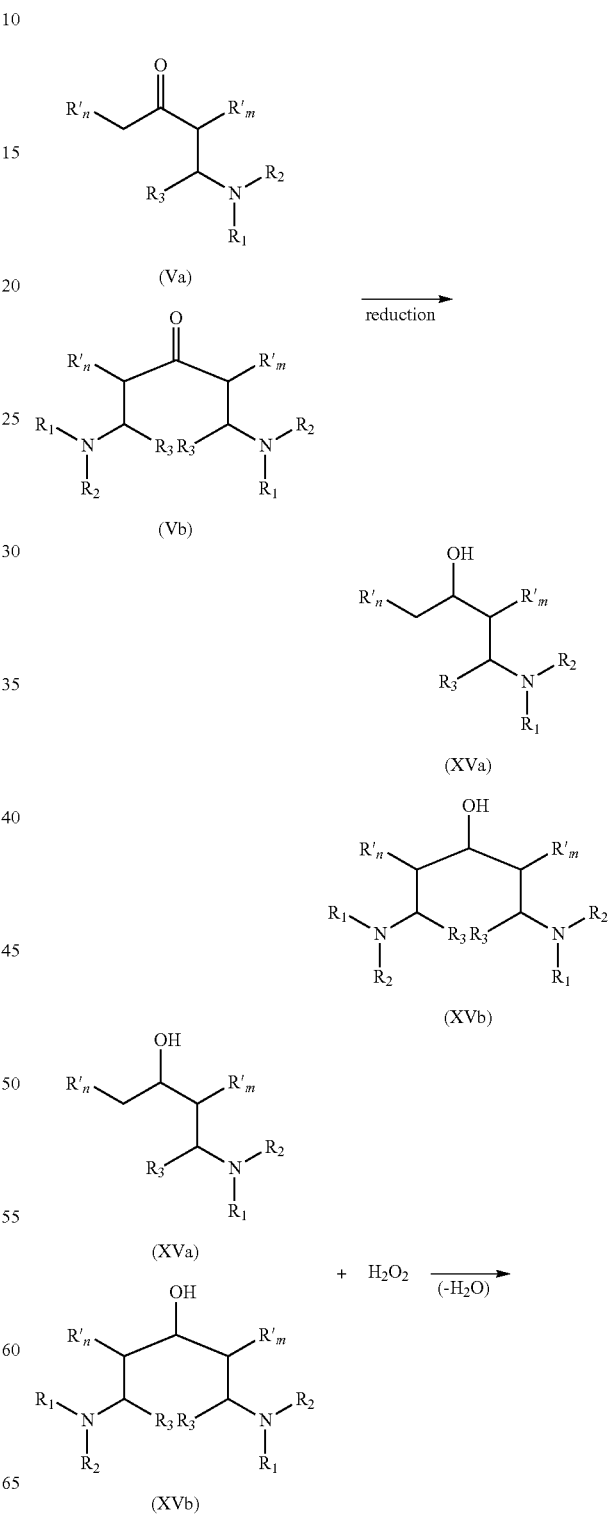

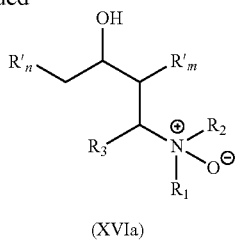

(XVIa)

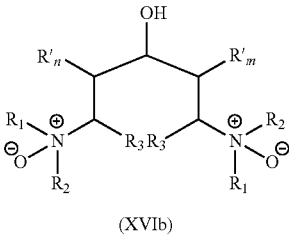

(XVIb)

In a first step, the ketone (Va) or (Vb) or a mixture thereof is reduced respectively to the alcohol derivative (XVa) or (XVb) or a mixture thereof.

As example of suitable reductants that can be used for this first step, one can mention $H_2$. In this case, the reaction must be conducted in the presence of a suitable transition metal (e.g. Fe, Ru, Co, Rh, Ir, Ni, Pd, Pt, Cu) based catalyst (for example Pd/C). The reaction can be carried out under a hydrogen pressure (typically from 1 atm to 200 bar) and at a temperature ranging from 15° C. to 400° C. Optionally, the reaction is conducted in the presence of an added solvent such as methanol, ethanol, isopropanol, tert-butanol, dioxane, dimethoxyethane, diglyme or a mixture thereof.

Another example of a suitable reductant for this first step is a secondary alcohol, preferably isopropanol which acts as a sacrificial reagent. In this case, the reaction requires the need of a metal based (e.g. Ni, Al, In, Ru, Zr) catalyst (e.g. aluminum isopropoxide $Al(O-i-Pr)_3$) and acetone is formed as by-product. Importantly acetone can be removed during the reaction thanks to distillation in order to displace equilibrium toward the formation of (XVa) and (XVb).

The second step consists in the oxidation using $H_2O_2$ of the tertiary amine group of the compound of formula (XVa) and/or the compound of formula (XVb) to form respectively the aminoxide derivative of formula (XVIa) and/or the aminoxide Gemini compound of formula (XVIb).

This second step can be carried out as described in part 4.1.

$R_1$, $R_2$ and $R_3$ have the same definitions as in part 2.2.

5—Making betaines and sultaines from Internal Ketones K1

5.1) Synthesis of dibetaine Twin-Tail amines and disultaine Twin-Tail amines

The end compound can be a dibetaine twin-tail amine, that is to say a twin-tail amine substituted by two betaine moieties.

The end compound can also be a disultaine twin-tail amine, that is to say a twin-tail amine comprising two sultaine moieties.

At least one dibetaine twin-tail amine can be obtained from at least one twin-tail di-tert-amino amine (that is to say a twin-tail amine that is itself substituted by two tert-amino groups) -which twin-tail di-tert-amino amine is itself previously obtained from at least one internal ketone K1 that is advantageously synthesized by the process P- by reacting said twin-tail di-tert-amino amine with a compound of formula X-Alk-$R_0$ wherein:
X is a leaving group,
Alk is an alkylene group, and
$R_0$ is —$CO_2M$ with M being an alkaline metal.
Methylene is preferred as the alkylene group Alk.
Na is preferred as the alkaline metal M.

The leaving group X is typically a halide such as Cl, Br or I, methylsulfate (—$SO_4Me$), sulfate (—$SO_4^-$), a sulfonate derivative such as methanesulfonate (—$O_3S$—$CH_3$), para-toluenesulfonate (—$O_3S$—$C_7H_7$) or trifluoromethane-sulfonate (—$O_3S$—$CF_3$).

At least one disultaine twin-tail amine can similarly be obtained from at least one twin-tail di-tert-amino amine which twin-tail di-tert-amino amine is itself previously obtained from at least one internal ketone K1 advantageously synthesized by the process P, by reacting said twin-tail di-tert-amino amine with a compound of formula X-Alk-$R_0$ wherein:
X is a leaving group,
Alk is an alkylene group, and
$R_0$ is —CH(OH)—$CH_2$—$SO_3M$ with M being an alkaline metal.

Preferred X, Alk and M to make the disultaine twin-tail amine are the same as the ones preferred to make the dibetaine twin-tail amine.

To make the dibetaine and/or the disultaine, at least one certain twin-tail amine of formula (III) is advantageously used as reactant, namely a twin-tail amine of formula (III$^{4'}$):

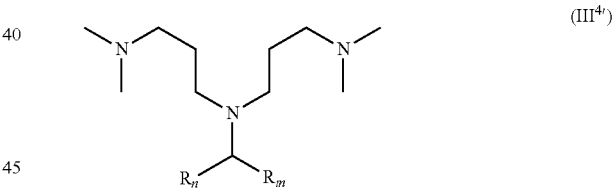

(III$^{4'}$)

wherein $R_n$ and $R_m$ have the same meaning as $R_n$ and $R_m$ of the internal ketone K1 of formula (I).

Then, at least one dibetaine of formula (XVIIa) and/or at least one disultaine of formula (XVIIb) can be prepared from at least one twin-tail amine of formula (III$^{4'}$) according to the following scheme:

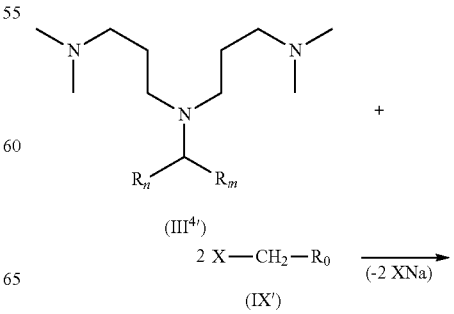

(III$^{4'}$)

2 X—$CH_2$—$R_0$ $\xrightarrow{(-2\,XNa)}$ (IX')

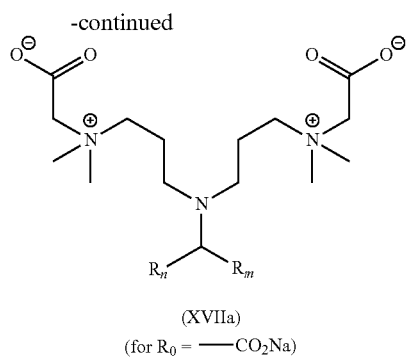

(XVIIa)

(for $R_0$ = —CO$_2$Na)

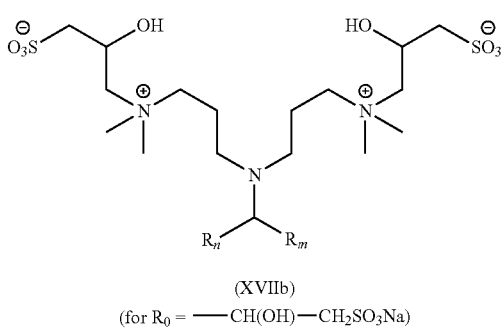

(XVIIb)

(for $R_0$ = —CH(OH)—CH$_2$SO$_3$Na)

In the above reaction scheme, X is as previously defined.

The twin-tail amine (III$^{4+}$) obtained according to part 1.1 from the internal ketone K1 (I) is reacted with the alkylating compound (IX') to afford the betaine (XVIIa) or the sultaïne (XVIIb) depending on the nature of (IX').

Betaine (XVIIa) is obtained when $R_0$ is —CO$_2$Na and sultaine (XVIIb) is obtained when $R_0$=—CH(OH)—CH$_2$—SO$_3$Na. A mixture of betaine and sultaine is obtained when using a mixture of reagents (IX') including at least one reagent wherein $R_0$ is —CO$_2$Na and at least one reagent wherein $R_0$=—CH(OH)—CH$_2$—SO$_3$Na.

The reaction is usually conducted by contacting the reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 and 9.5. This adjustment can be done by adding required amounts of concentrated NaOH and/or HCl aqueous solutions to the reaction medium during the course of the reaction.

5.2) Synthesis of betaine Derivatives and sultaine Derivatives, Especially of betaine Gemini Derivatives and sultaine Gemini Derivatives The end product can be a betaine Gemini compound or a sultaine Gemini compound. Typically, the betaine or sultaine Gemini compound comprises a central hydroxyl group which, in a two-dimensional representation of the formula of this compound, can form a symmetry axis provided some conditions are met on the nature of its substituents, as will immediately be made apparent from what follows.

At least one dibetaine and/or at least one disultaine can be obtained from at least one ketone having one or both of its carbonyl-adjacent carbon atoms substituted by an amine-containing group, in particular from at least one ketone of formula (Va) and/or at least one ketone of formula (Vb), the preparation of which from the internal ketone K1 of formula (I) has been described in part 1.2.

At least one dibetaine and/or at least one disultaine can be obtained from at least one ketone having both of its carbonyl-adjacent carbon atoms substituted by a tert-amino-containing group, in particular from at least one ketone of formula (Vb), the preparation of which from the internal ketone K1 of formula (I) has already been described in part 1.2.

At least one monobetaine and/or at least one monosultaine can be obtained from at least one ketone having one (and only one) of its carbonyl-adjacent carbon atoms substituted by a tert-amino-containing group, in particular from at least one ketone of formula (Va), the preparation of which from the internal ketone K1 of formula (I) has already been described in pad 1.2.

To this effect, the following reaction scheme can be followed:

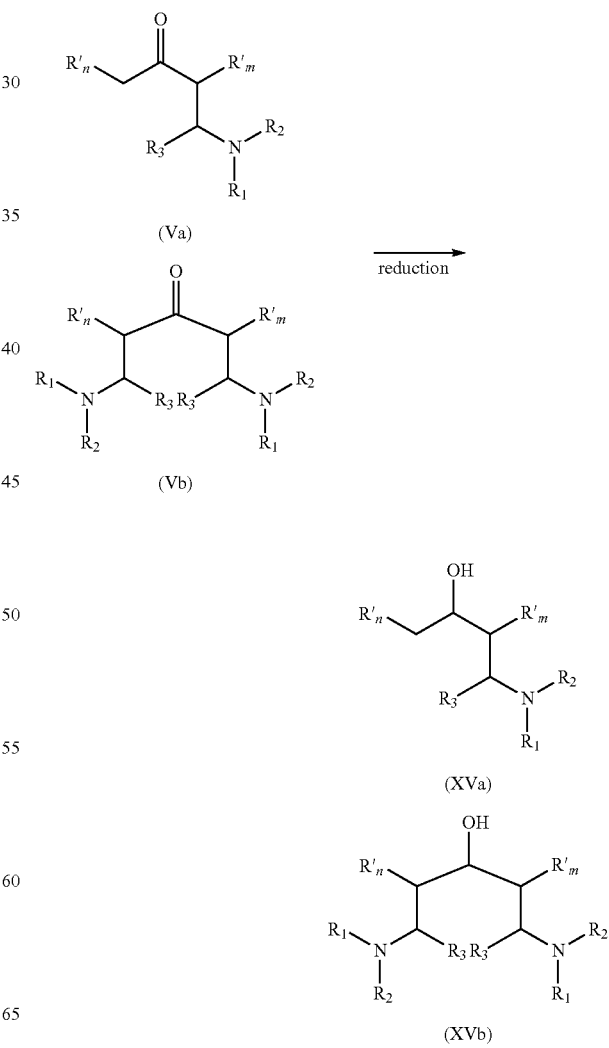

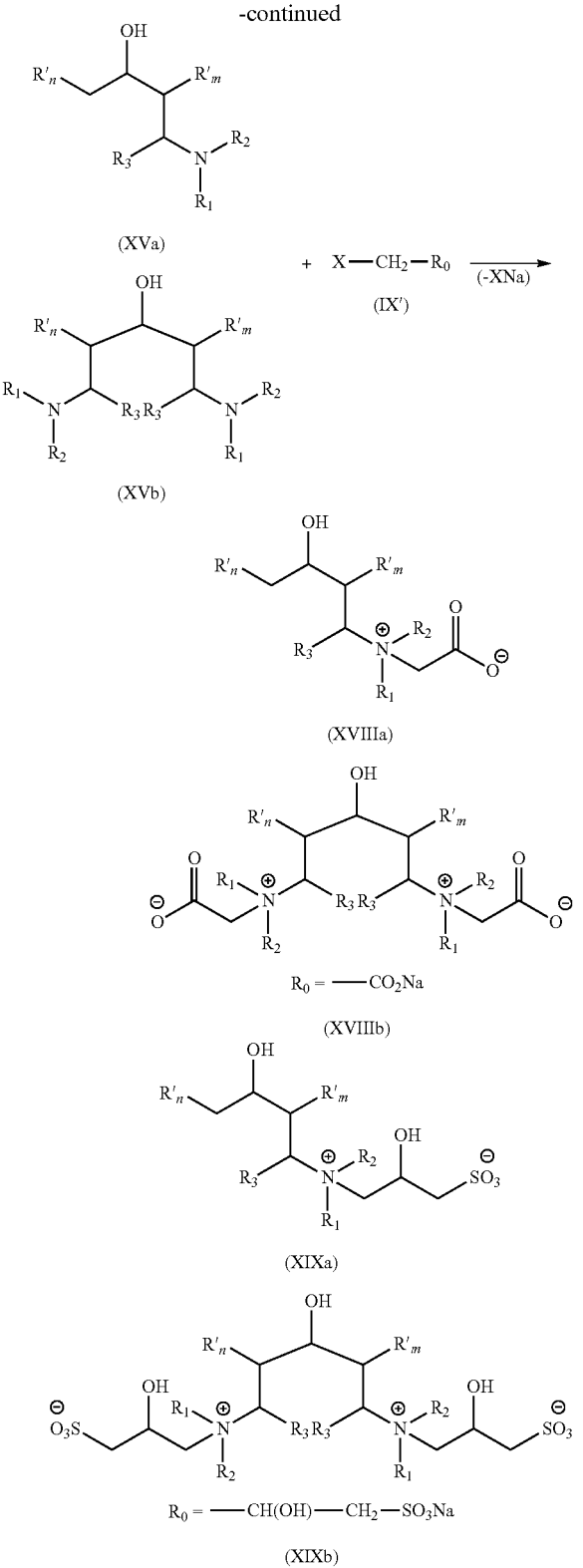

(XVa)

(XVb)

(XVIIIa)

(XVIIIb)
$R_0 = -CO_2Na$ (XIXa)

(XIXb)
$R_0 = -CH(OH)-CH_2-SO_3Na$

The first step is identical as in part 4.2.

The second step is carried out as in part 5.1.

Betaine (XVIII) or sultaine (XIX) is obtained depending on the nature of $R_0$ in the alkylating agent (IX').

$R_1$, $R_2$ and $R_3$ have the same definition as in part 2.2.

6—Making Anionic Surfactants from Internal Ketones K1

Synthesis of dicarboxylate Salt Derivatives

The end compound can be an anionic surfactant.

For example, it can be a dicarboxylate salt derivative of formula

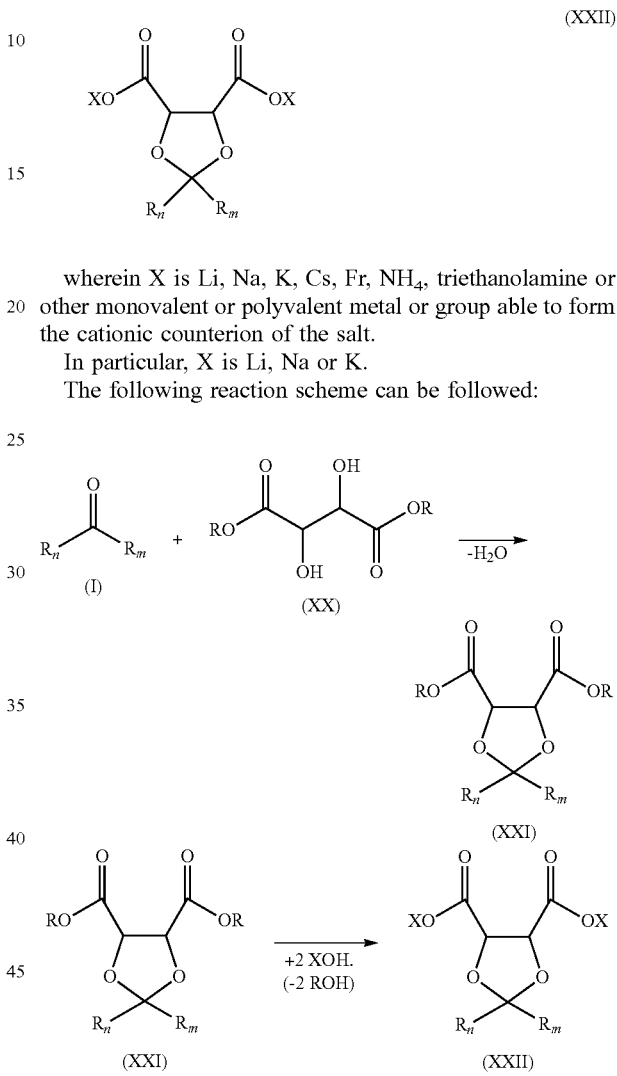

(XXII)

wherein X is Li, Na, K, Cs, Fr, $NH_4$, triethanolamine or other monovalent or polyvalent metal or group able to form the cationic counterion of the salt.

In particular, X is Li, Na or K.

The following reaction scheme can be followed:

(I)

(XX)

(XXI)

(XXI)

(XXII)

In a first step, at least one ketone K1 of formula (I) as previously defined is condensed with at least one diester (XX) derived from tartaric acid in which R denotes a linear or branched alkyl radical containing from 1 to 6 carbon atoms.

The reaction is realized by contacting the ketone and the diester in a reaction zone at a temperature ranging from 15° C. to 400° C. The reaction can be optionally carried out in the presence of an added solvent such as toluene, xylene, dioxane, diglyme, hexanes, petroleum ether, DMSO or a mixture thereof.

In a preferred embodiment, an acid catalyst (either Bronsted or Lewis acid) is employed to accelerate the reaction. One can mention for example $H_2SO_4$, HCl, triflic acid, p-toluenesulfonic acid, $AlCl_3$, metal triflate compounds such as aluminium triflate, bismuth triflate, heterogeneous solid acids such as Amberlyst resins and zeolites.

The water generated during the reaction can be trapped thanks to a Dean-Stark apparatus in order to displace the reaction equilibrium toward the formation of intermediate product (XXI).

At the end of the reaction, this intermediate (XXI) can be isolated after solvent and catalyst removal using standard work-up techniques well known by the skilled person of the art so that no further detail needs to be given here.

In a second step, the ketal diester (XXI) is hydrolysed by conducting the reaction in a basic aqueous XOH or X(OH)$_2$ solution (X as above defined, in particular X=Li, Na, K, Cs, Mg, Ca) at temperature ranging from 15° C. to 400° C. to afford the final ketal carboxylate product (XXII) along with R—OH as by-product.

7—Making Non-Ionic Surfactants from Internal Ketones K1

The end compound can be a non-ionic surfactant.

7.1) First Synthesis of Non-Ionic Surfactants

The end compound can be a compound of formula (XXV)

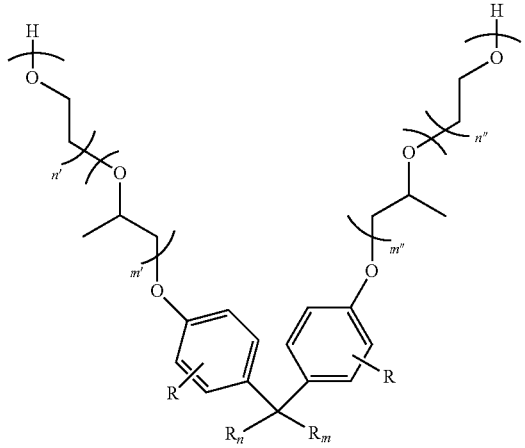

(XXV)

wherein:

m', m", n' and n" are integers ranging from 0 to 40 with the proviso that at least one of m', m", n' and n" is of at least 1, and m'+m"+n'+n" ranges preferably from 2 to 40, possibly from 4 to 20, $R_m$ and $R_n$ are as defined in part 1.1, R is nil (meaning that there is no substituent on the benzene rings) or R is at least one $C_1$-$C_{24}$ alkoxy or a linear or branched $C_1$-$C_{24}$ hydrocarbon group, which alkoxy or hydrocarbon group can be optionally interrupted and/or substituted by one or more heteroatoms or heteroatom containing groups.

By specifying that R can be "at least one linear or branched hydrocarbon group", it is intended to denote that the benzene rings of compound (XXV) can be substituted not only by one substituent but also by several one linear or branched hydrocarbon substituents.

Two examples of possible R substituents are methyl and methoxy.

The following reaction scheme can be followed:

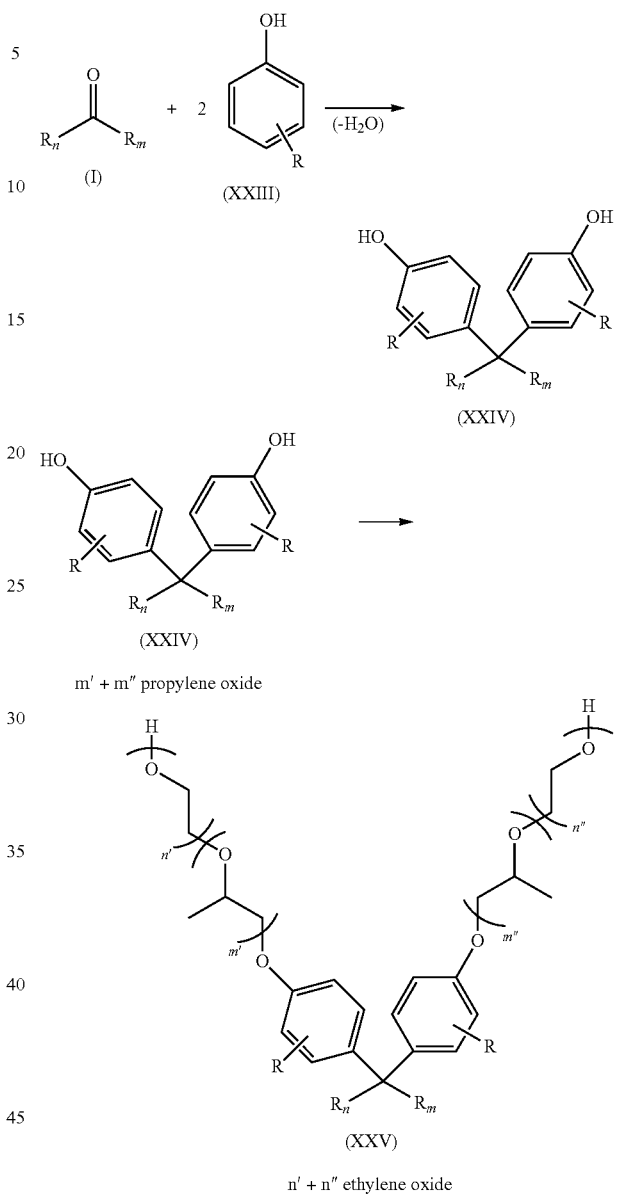

Accordingly, in a first step, at least one ketone K1 of formula (I) is first condensed with 2 equivalents of a substituted or unsubstituted phenolic compound (XXII) (e.g. when R is nil, (XXII) is phenol, while when R is methyl or methoxy, (XXII) is respectively cresol or guaiacol) in order to afford the bi-phenolic derivative (XXIV).

The reaction can be carried out by contacted both reactants in a reaction zone at a temperature ranging from 15° C. to 400° C. optionally in the presence of an added solvent. An excess of the phenolic derivative (XXIII) can be used for this reaction and the reactant in excess can be removed later during the subsequent work-up and recycled.

An acid catalyst (either Bronsted or Lewis acid) can be employed to accelerate the reaction. One can mention for example $H_2SO_4$, HCl, triflic acid, p-toluenesulfonic acid, $AlCl_3$, metal triflate compounds such as aluminium triflate and bismuth triflate, heterogeneous solid acids (such as Amberlyst resins, zeolites, etc.

Water generated during this step can be trapped thanks to a Dean-Stark apparatus is order to drive the reaction equilibrium toward the desired product (XXIV).

The intermediate product (XXIV) can be isolated using standard work-up techniques well known by the skilled person of the art so that no further detail needs to be given here.

In a second step, the di-phenolic derivative (XXIV) is condensed with m'+m" equivalents of propylene oxide and/ or by, possibly followed by, n'+n" equivalents of ethylene oxide using standard conditions for alkoxylation of di-phenolic derivatives in order to afford the non-ionic surfactant (XXV).

Other non-ionic surfactants than (XXV) can be prepared according to the same reaction scheme but using another aromatic alcohol than (XXIII) as reagent.

As examples of other aromatic alcohols, one can mention naphthols and aromatic diols such as catechol and resorcinol.

7.2) Second Synthesis of Non-Ionic Surfactants

The end compound can be a non-ionic surfactant of formula (XXVIIa)

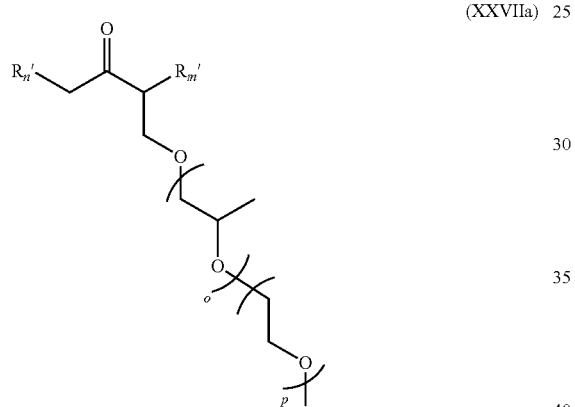

(XXVIIa)

or a non-ionic surfactant of formula (XXVIIb)

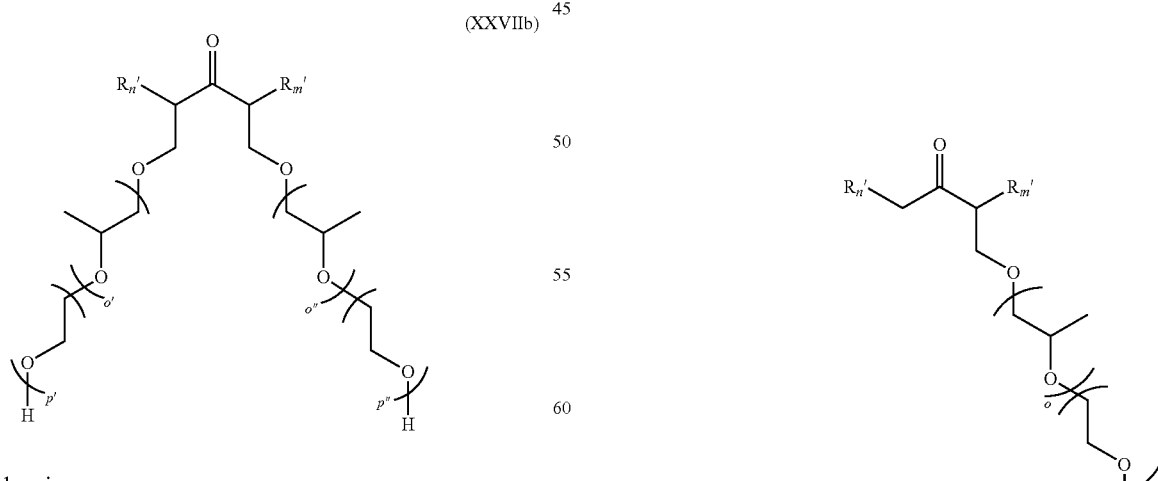

(XXVIIb)

wherein:

$R'_m$ and $R'_n$ represent an aliphatic group, generally a $C_2$-$C_{26}$ aliphatic group, very often a $C_2$-$C_{18}$ group, often a $C_5$-$C_{16}$ group, o, o', o", p, p' and p" are as defined hereinafter.

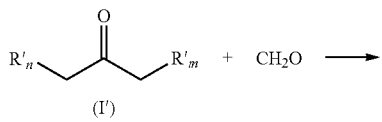

(I')

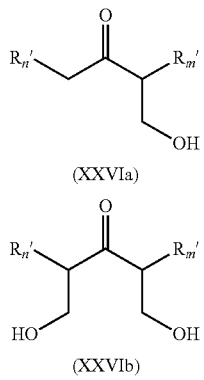

(XXVIa)

(XXVIb)

7.3) Third Synthesis of Non-Ionic Surfactants

The end compound can be a compound of formula (XXIX)

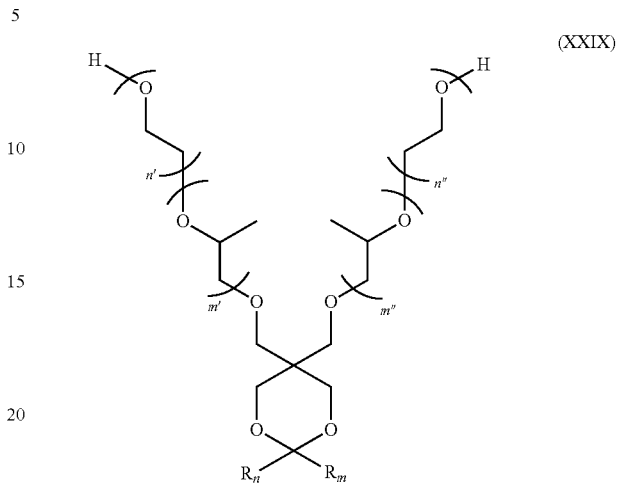

(XXIX)

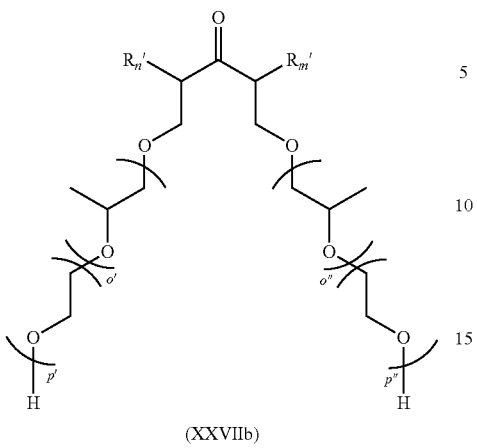

(XXVIIb)

In the above scheme, "1) m propylene oxide | 2) n ethylene oxide" should be broadly understood, not implying that both propoxylation and ethoxylation must take place (otherwise said, m or n can be equal to 0), a fortiori not implying that propoxylation must take place before ethoxylation, although this is an embodiment that may be preferred.

In a first step, at least one ketone K1 of formula (I') is condensed with formaldehyde ($CH_2O$). The condensation takes advantageously place in a reaction zone at a temperature ranging from −20° C. to 400° C. The reaction can be carried out in the presence of a basic catalyst, such as for example NaOH, KOH, MgO, $Na_2CO_3$, NaOMe, NaOEt, tBuOK or $NEt_3$ wherein Me is methyl, Et is ethyl and Bu is butyl. The reaction can optionally be carried out in a solvent such as methanol, ethanol, isopropanol, DMSO, THF, methyltetrahydrofuran, toluene, a xylene, water, dioxane or a mixture thereof.

For this first reaction step, formaldehyde can be used in excess and the reactant in excess can be recovered and recycled.

The aldol products (XXVIa), (XXVIb) or their mixture can be isolated using standard work-up techniques well known by the skilled person of the art.

In the second step, at least one product (XXVIa) and/or (XXVIb) is/are condensed with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactants (XXVIIa) and/or (XXVIIb).

In the above equation scheme, m and n are integers ranging from 0 to 40 but m and n cannot be both equal to 0.

o, p, o', p', o" and p" are integers ranging from 0 to 40 and the following equalities must be respected:

o+o'+o"=m p+p'+p"=n wherein:

$R_n$ and $R_m$ are as defined in part 1.1,
m', m", n' and n" are as defined hereinafter.

To this end, in a first step, at least one internal ketone K1 of formula (I) is condensed with pentaerythritol to afford at least one intermediate (XXVIII).

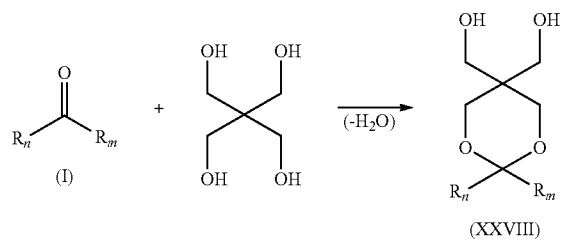

(XXVIII)

This reaction is advantageously carried out by contacted both reactants in a reaction zone at a temperature ranging from 15° C. to 400° C. The reaction can be optionally carried out in the presence of an added solvent such as toluene, xylene, dioxane, diglyme, hexane, petroleum ether, DMSO or a mixture thereof.

In a preferred embodiment, an acid catalyst (either Bronsted or Lewis acid) is employed to accelerate the reaction. One can mention for example: $H_2SO_4$, HCl, triflic acid, p-toluenesulfonic acid, $AlCl_3$, metal triflate compounds such as aluminium triflate, bismuth triflate, heterogeneous solid acids such as Amberlyst resins, zeolites, etc.

The water generated during the reaction can be trapped thanks to a Dean-Stark apparatus in order to displace the reaction equilibrium toward the formation of the at least one intermediate (XXVIII).

At the end of the reaction, this intermediate (XXVIII) can be isolated after solvent and catalyst removal using standard work-up techniques well known by the skilled person of the art so that no further detail needs to be given here.

In the second step, the at least one intermediate (XXVIII) is condensed with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactant (XXIX)

The reaction taking place in the second step can be represented as follows:

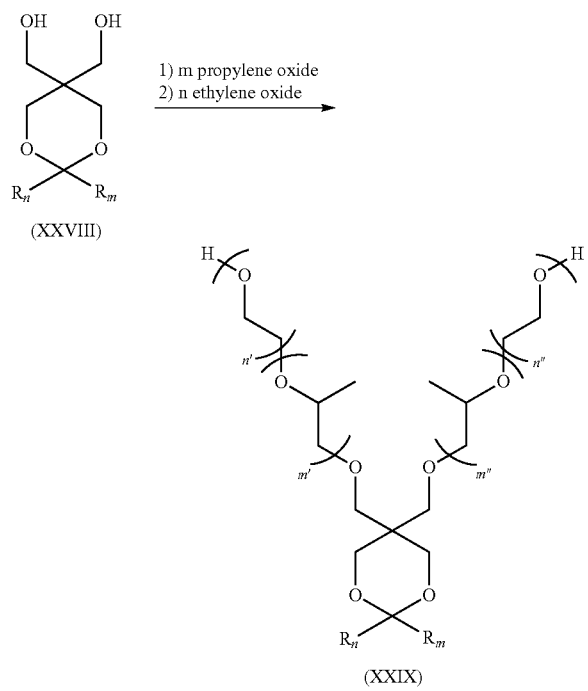

In the above reaction scheme, "1) m propylene oxide | 2) n ethylene oxide" should be broadly understood, not implying that both propoxylation and ethoxylation must take place (otherwise said, m or n can be equal to 0), a fortiori not implying that propoxylation must take place before ethoxylation, although this is an embodiment that may be preferred.

As a matter of fact, in the above reaction scheme, m and n are integers ranging from 0 to 40 provided at least one of m and n is of at least 1.

m', m", n' and n" are integers ranging from 0 to 40 and the following equalities must be respected:

m'+m"=m n'+n"=n

8—Making Intermediates and Monomers from Internal Ketones K1

8.1) Synthesis of Beta Diketones

The at least one end compound can be a beta diketone of formula (XXXIa) and/or a beta diketone of formula (XXXIb), such as the reaction products of the following reaction involving at least one internal ketone K1 of formula (I'):

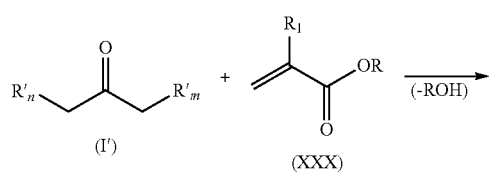

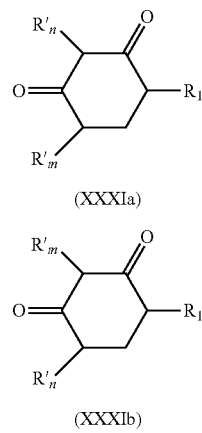

Accordingly, at least one ketone K1 of formula (I') with $R_m$ and $R_n$ as previously defined is reacted with at least one acrylate derivative (XXX) to obtain at least one diketone (XXXIa) and/or at least one diketone (XXXIb).

In the above reaction scheme, the substituent R is selected from a linear or branched hydrocarbon radical having from 1 to 24 carbon atoms which can be optionally substituted and/or interrupted by one or more heteroatoms or heteroatom containing groups. For example, R can be selected from $-CH_3$, $-CH_2CH_3$, propyl, isopropyl, butyl, sec-butyl, isobutyl and tert-butyl.

The substituent $R_1$ is selected from hydrogen and a linear or branched hydrocarbon radical having from 1 to 24 carbon atoms which can be optionally substituted and/or interrupted by one or more heteroatoms or heteroatom containing groups. For example, $R_1$ can be H, methyl, ethyl, propyl, isopropyl, butyl, sec-butyl, isobutyl or tert-butyl.

The reaction zone takes advantageously place at a temperature ranging from 15° C. to 400° C.

At least one equivalent relative to the ketone K1 of formula (I') of a base may be required for the reaction to occur. As example of suitable bases to carry out the reaction, one can mention NaOMe, tert-BuOK, NaOEt, KOH or NaOH.

During the course of the reaction an alcohol R—OH is generated which can optionally be distilled off from the reaction mixture.

In addition, a suitable solvent can be used for the reaction such as for example methanol, ethanol, isopropanol, THF, DMSO, methyltetrahydrofuran, dioxane or diglyme.

At the end of the reaction, the at least one diketone compound (XXXIa) and/or the at least one diketone compound (XXXIb) are possibly obtained in their deprotonated form so that an acidic quench is needed to recover the neutral derivatives (XXXIa) and/or (XXXIb).

8.2) Synthesis of a First Monomer

The at least one end compound can be a compound of formula (XXXIII). Such a compound, which contains an ethylenic carbon-carbon double bond, is suitable to undergo a radical polymerization.

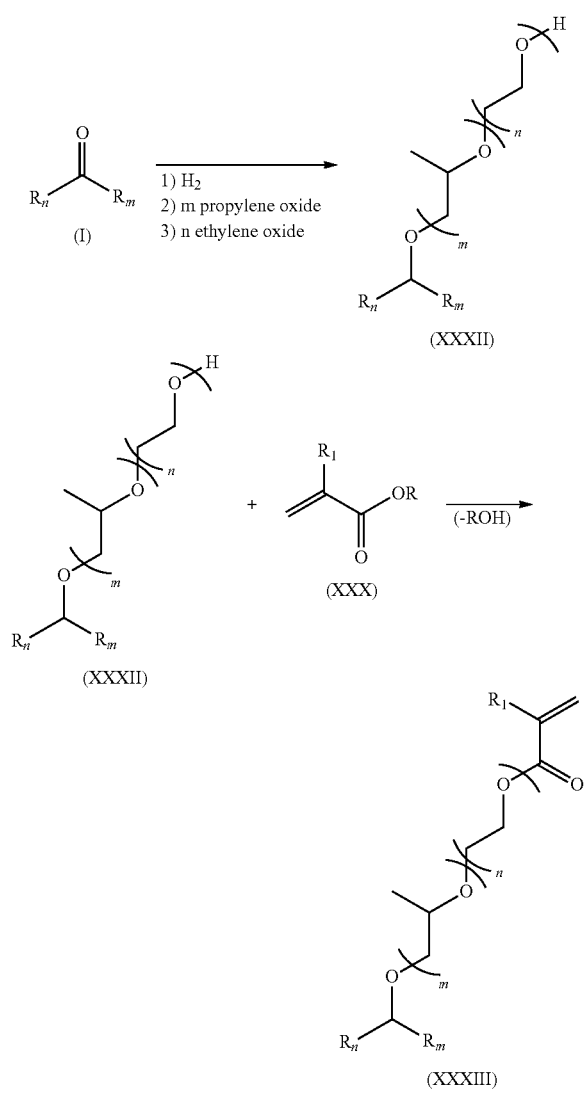

$R_m$ and $R_n$ are as defined in part 1.1, and m and n are integers ranging from 0 to 40 but m and n cannot be both equal to 0.

R and $R_1$ have the same meaning as in part 8.1.

According to the above reaction scheme, at least one ketone K1 of formula (I) is hydrogenated using standard hydrogenation conditions, then condensed with m equivalents of propylene oxide and/or n equivalents or ethylene oxide (e.g. with m equivalents of propylene oxide followed by n equivalents of ethylene oxide).

Standard conditions for secondary alcohols alkoxylations are generally used in order to afford the at least one intermediate (XXXII).

The intermediate (XXXII) is then reacted with at least one acrylate derivative (XXX) according to a transesterification reaction in order to afford at least one other acrylate derivative (XXXIII).

This last reaction is advantageously carried out by contacting both reactants in a reaction zone at a temperature ranging from 15° C. to 400° C.

The reaction can be catalysed either by acids or by bases. As example of suitable acids, one can mention $H_2SO_4$, HCl, triflic acid, p-toluenesulfonic acid, $AlCl_3$, metal triflate compounds such as aluminium triflate, bismuth triflate, heterogeneous solid acids such as Amberlyst resins, zeolites etc.

As examples of suitable bases, one can mention NaOH, KOH, MgO, $Na_2CO_3$, NaOMe, NaOEt, tBuOK or $NEt_3$ wherein Me is methyl, Et is ethyl and tBu is tert-butyl.

The reaction can be carried out in a suitable solvent such as methanol, ethanol, isopropanol, DMSO, THF, methyltetrahydrofuran, toluene, xylenes, water, dioxane or a mixture thereof.

The acrylate derivative (XXX) can be added progressively in the reaction medium in order to avoid side-polymerization to occur.

8.3) Synthesis of a Second Monomer

The at least one end compound can be a compound of formula (XXXIV)

Such a compound, which also contains an ethylenic carbon-carbon double bond, is likewise suitable to undergo a radical polymerization.

It can be prepared from a certain twin-tail amine of formula (III), namely an a primary of secondary twin-tail amine of formula (III$^{5'}$)

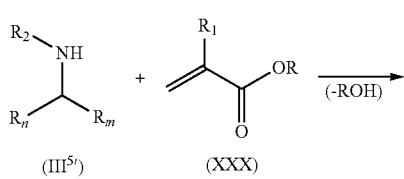

wherein:

$R_m$ and $R_n$ are as defined in part 1.1;

$R_2$ is selected from hydrogen or a linear or branched hydrocarbon radical having 1 to 24 carbon atoms which can be optionally substituted and/or interrupted by one or more heteroatoms or hereroatom containing groups; for example, $R_2$ can be selected from H, —$CH_3$, —$CH_2CH_3$, propyl, isopropyl, butyl, sec-butyl, isobutyl and tert-butyl.

At least one amine (III$^{5'}$) prepared according to part 1.1 is reacted with at least one acrylate derivative (XXX) under suitable conditions that prevent conjugate addition to occur in order to afford at least one acrylamide (XXXIV).

The reaction scheme is as follows:

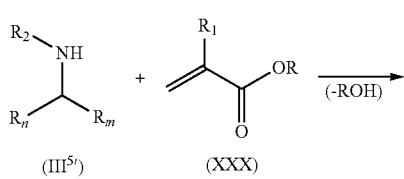

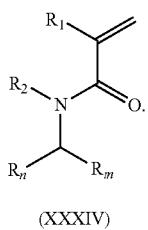

(XXXIV)

In compounds (XXX) and (XXXIV), R and $R_1$ have the same meaning as in part 8.1.

The reaction is advantageously carried out by contacting both reactants in a reaction zone at a temperature ranging from 15° C. to 400° C.

The reaction can be catalysed by acids or bases. As example of suitable acids one can mention $H_2SO_4$, HCl, triflic acid, p-toluenesulfonic acid, $AlCl_3$, metal triflate compounds (such as aluminium triflate, bismuth triflate), heterogeneous solid acids such as Amberlyst resins, zeolites, etc. As examples of suitable bases, one can mention NaOH, KOH, MgO, $Na_2CO_3$, NaOMe, NaOEt, tBuOK, $NEt_3$ etc.

The reaction can be carried out in a suitable solvent such as methanol, ethanol, isopropanol, DMSO, THF, methyltetrahydrofuran, toluene, xylenes, water, dioxane or a mixture thereof.

As an alcohol ROH is generated during the reaction as a side product, it can be removed thanks to distillation in order to drive the reaction toward the desired product (XXXIV).

The acrylate derivative (XXX) can be added progressively in the reaction medium in order to avoid side-polymerization to occur.

8.4) Synthesis of a Branched Fatty Acid

The end compound can be a branched fatty acid of formula (XXXV), as obtainable by the following reaction:

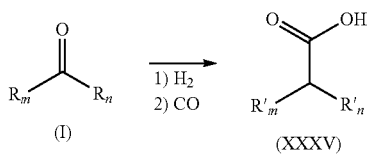

In a first stage, at least one ketone K1 of formula (I) with $R_m$ and $R_n$ being defined as in part 1.1 is hydrogenated to afford the corresponding secondary alcohol. Standard hydrogenation conditions can be used.

This alcohol is then engaged in a carbonylation reaction to afford at least one end product (XXXV).

The carbonylation reaction is advantageously carried out by reacting the secondary alcohol under a CO pressure (typically from 1 atm to 200 bar), in a reaction zone at a temperature usually ranging from 15° C. to 400° C.

The reaction can be optionally carried out in the presence of a suitable solvent and the skilled person of the art will choose the most suitable solvent. Importantly, the reaction can be catalysed by transition metal based catalysts (for example Co, Rh, Ir and Pd based homogeneous catalyst).

Usually, a halide based promoter is necessary for the reaction to occur. Preferably, the promoter is an iodide, such as HI.

Importantly, during the reaction significant isomerization may occur and mixture of isomeric products (XXXV) may be obtained having their alkyl substituents $R'_m$ and $R'_n$ different from the initial alkyl substituents $R_m$ and $R_n$ present in the starting ketone K1 of formula (I). Thus, in formula (XXXV) specifically, $R'_m$ and $R'_n$ fall under the same general definition of $R_m$ and $R_n$ although being possibly specifically different from initial $R_m$ and $R_n$ of starting ketone K1 of formula (I).

8.5) Synthesis of Polyamines

The end compound can be a polyamine, especially a polyamine of formula (XXXVII):

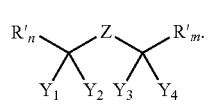

(XXXVII)

Such a polyamine can be prepared using at least one internal ketone K1 of formula (I') as starting material, with $R'_m$ and $R'_n$ being defined as in part 1.2, according to the following reaction scheme:

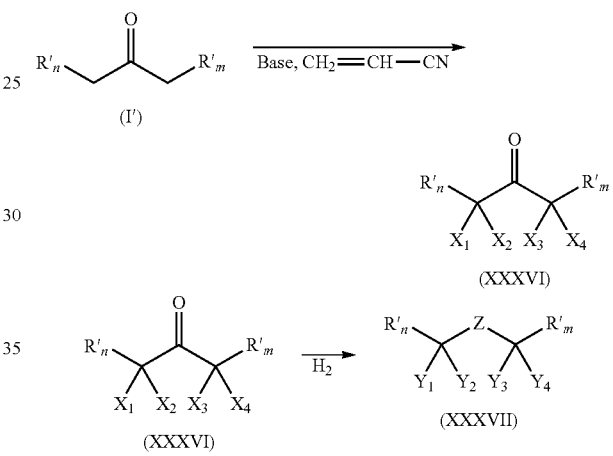

$X_1$, $X_2$, $X_3$ and $X_4$ independently represent a hydrogen atom or —$CH_2$—$CH_2$—CN but all cannot be hydrogen, meaning that at least one of $X_1$, $X_2$, $X_3$ and $X_4$ is —$CH_2$—$CH_2$—CN.

$Y_1$, $Y_2$, $Y_3$ and $Y_4$ independently represent a hydrogen atom or —$CH_2$—$CH_2$—$CH_2$—$NH_2$ but all cannot be hydrogen, meaning that at least one of $Y_1$, $Y_2$, $Y_3$ and $Y_4$ is —$CH_2$—$CH_2$—$CH_2$—$NH_2$.

Z can be either a carbonyl group (C=O) or a carbinol (CH—OH) group or a mixture thereof.

Thus, at least one ketone K1 of formula (I') is first condensed with acrylonitrile to afford at least one intermediate of formula (XXXVI).

The reaction is advantageously carried out by contacting both reactants in a reaction zone at a temperature ranging generally from 15° C. to 400° C. and in the presence of an optional solvent such as methanol, ethanol, isopropanol, DMSO, THF, methyltetrahydrofuran, toluene, a xylene, water, dioxane or a mixture thereof.

The reaction can be catalysed by a suitable base such as for example NaOH, KOH, MgO, $Na_2CO_3$, NaOMe, NaOEt, tBuOK or $NEt_3$.

Optionally and possibly preferably, the reaction is carried out by adding acrylonitrile progressively in the reaction medium in order to avoid side polymerizations, and acrylonitrile can be used in stoichiometric excess. The acrylonitrile in excess can be recovered and recycled.

Mixture of products (XXXVI) with different substituents $X_n$ (n=1 to 4) can be obtained.

In a second step, at least one (poly)nitrile derivative (XXXVI) is hydrogenated to afford the at least one corresponding (poly)amine (XXXVII). Usually, standard conditions for nitrile hydrogenation are used, for example under hydrogen pressure ranging from 1 atm to 200 bar, at a temperature ranging from 15° C. to 400° C., in the presence of an optional solvent and using advantageously a transition metal based catalyst (e.g. Nickel Raney).

A mixture of products (XXXVII) with different Yn (n=1 to 4) and Z groups can be obtained.

Special Embodiments of the Method M

In certain special embodiments of the invented method M:

when the internal ketone K1 is caused to react by being subjected to a hydrogenation reaction to obtain a secondary alcohol, the so-obtained secondary alcohol may be an intermediate that is in turn caused to react in accordance with a single or multiple reaction scheme that does not include a dehydration reaction that would convert said internal secondary alcohol into an internal olefin as an other intermediate or as the end compound;

the end compound may differ from an α-sulfocarbonyl compound C1* of of formula (1)

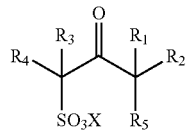

(1)

from an α-sulfocarbonyl compound C2* of formula (2)

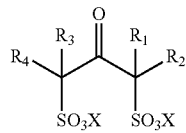

(2)

and from a mixture thereof, wherein in above formulae (1) and (2)

$R_1$, $R_3$ and $R_5$, which may be the same or different at each occurrence, are hydrogen or a linear or branched alkyl chain having 1 to 20 carbon atoms, $R_2$ and $R_4$, which may be the same or different at each occurrence, are a linear or branched alkyl group having 4 to 24 carbon atoms and in which the alkyl chain may comprise one or more cycloaliphatic groups, and X is H or a cation forming a salt with the sulfonate group;

the end compound may differ from a surfactant C3* of formula (3)

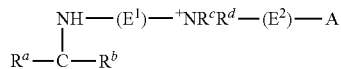

(3)

from a diamine C4* of formula (4)

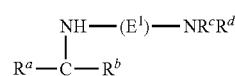

(4)

and from a mixture thereof, wherein in above formulae (3) and (4)

each of $R^a$ and $R^b$, which are identical or different, is a linear or branched, saturated or unsaturated, hydrocarbon chain that may be interrupted and/or substituted by at least a monocyclic or polycyclic group each of $R^c$ and $R^d$, which are identical or different, is a linear or branched, alkyl chain having 1 to 10 carbon atoms each of ($E^1$) and ($E^2$) is a divalent hydrocarbon radical linear or branched, not substituted or substituted, A is: a carboxylate group —COO$^-$, optionally in all or part in its protonated form —COOH; or a sulfonate group —SO$_3$, optionally in all or part in its protonated form —SO$_3$H;

the end compound may differ from a secondary alcohol C5; it may notably differ from a secondary alcohol C5* comprising as sole functional group(s) an internal alcohol group and, optionally in addition, one or more alkene and/or alkyne groups

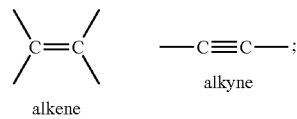

the end compound may differ from an internal olefin C6*;

the end compound may also differ from an α-sulfocarbonyl compound C7*

The method M differs advantageously from the methods that are disclosed in International application PCT/EP2016/060106 filed on May 4, 2016, in International application PCT/EP2016/060070 filed on May 4, 2016, in European patent application 16305409.1 filed on Apr. 8, 2016, in European patent application 16305410.9 filed on Apr. 8, 2016 and in European patent application 16306069.2 filed on Aug. 19, 2016. The whole content of all these applications is herein incorporated for all purposes, especially for disclaiming purposes, if useful.

Valuable Compounds Preparable by the Method M

It is a last object of the present invention to provide new valuable compounds, with a particular interest for surfactants.

This last object of the present invention is achieved by a variety of compounds, notably surfactants, susceptible of being prepared by the method M as above described.

Many of these compounds can be characterized by their twin-tail or Gemini structure.

Thus, the present invention concerns also:

a compound of formula (III) as previously described, in particular a compound of formula (III'), a compound of formula (III''), a compound of formula (III$^{3'}$), a compound of formula (III$^{4'}$) or a compound of formula (III$^{5'}$) as previously described;

a compound of formula (Va) as previously described, a compound of formula (Vb) as previously described or a mixture thereof;

a compound of formula (VII) as previously described;
a compound of formula (VIIIa) as previously described, a compound of formula (VIIIb) as previously described or a mixture thereof;
a compound of formula (X) as previously described;
a compound or a mixture of compounds of general formula (XIa) as previously described;
a compound or a mixture of compounds of general formula (XIb) as previously described;
a compound of a mixture of compounds of general formula (XII) as previously described;
a compound of a mixture of compounds of general formula (XIIIa) as previously described;
a compound of a mixture of compounds of general formula (XIIIb) as previously described;
a compound of formula (XIV) as previously described;
a compound of formula (XVa) as previously described, a compound of formula (XVb) as previously described or a mixture thereof;
a compound of formula (XVIa) as previously described, a compound of formula (XVIb) as previously described or a mixture thereof;
a compound of formula (XVIIa) as previously described;
a compound of formula (XVIIb) as previously described;
a compound of formula (XVIIIa) as previously described, a compound of formula (XVIIIb) as previously described or a mixture thereof;
a compound of formula (XIXa) as previously described, a compound of formula (XIXb) as previously described or a mixture thereof;
a compound of formula (XXI) as previously described;
a compound of formula (XXII) as previously described;
a compound of formula (XXIV) as previously described;
a compound of formula (XXV) as previously described;
a compound of formula (XXVIa) as previously described, a compound of formula (XXVIb) as previously described or a mixture thereof;
a compound of formula (XXVIIa) as previously described, a compound of formula (XXVIIb) as previously described or a mixture thereof;
a compound of formula (XXVIII) as previously described;
a compound of formula (XXIX) as previously described;
a compound of formula (XXXIa) as previously described, a compound of formula (XXXIb) as previously described or a mixture thereof;
a compound of formula (XXXII) as previously described;
a compound of formula (XXXIII) as previously described;
a compound of formula (XXXIV) as previously described;
a compound or a mixture of compounds of general formula (XXXV) as previously described;
a compound or or a mixture of compounds of general formula (XXXVI) as previously described; and
a compound or or a mixture of compounds of general formula (XXXVII) as previously described.

Summary of the Advantages of the Present Invention

The process P of the present invention thus offers an easy access to internal ketones K1. The process P yields the desired ketones in high yield with only minor amounts (if at all) of undesired by-products being obtained and which can be easily separated from the reaction mixture.

The internal ketones K1 may be separated from the reaction mixture by convenient and economic processes and the catalytic material can be used for several catalytic cycles without significant deterioration of catalytic activity.

As thoroughly shown, the internal ketones K1 are versatile starting materials that can be easily converted into a variety of valuable end compounds through the method M.

The method M of the present invention, since it is based on the process P, thus likewise offers an easier access to these compounds.

Many end compounds obtainable by the method M are useful as surfactants.

Many other compounds obtainable by the method M are useful as intermediates that can in turn be converted into valuable end compounds like surfactants.

Should the disclosure of any patents, patent applications, and publications which are incorporated herein by reference conflict with the description of the present application to the extent that it may render a term unclear, the present description shall take precedence.

The following examples further explain the present invention.

EXAMPLES

Example 1

Ketonization of $C_8$-$C_{18}$ Fatty Acids Cut Using Magnetite Fe3O4 as the Catalyst The reaction is carried out under an inert atmosphere of argon.

In a 750 mL reactor equipped with a mechanical stirrer, a Dean-Stark apparatus to trap water generated during the reaction and an addition funnel, are dispensed 40 g of product C15-C35 ketones (made through a preliminary ketonization of the starting C8-C18 fatty acids) and 9.3 g (0.040 mole) of magnetite Fe3O4.

The addition funnel of the reactor is filled with 200 g (0.970 mole) of melted fatty acids (C8: 7 wt %, C10: 8 wt %, C12: 48 wt %, C14: 17 wt %, C16: 10 wt %, C18: 10 wt %).

The reaction mixture is then heated at 330° C. under stirring (500 rpm) and 200 g (0.970 mole) of the melted fatty acids is slowly introduced into the reactor such that the temperature of the reaction medium doesn't fall down below 320° C. (for example with an addition flow rate of around 25 g fatty acids/hour).

Practically this can be done also through the successive slow additions (1 hour per addition) of 4 portions of 50 g (60 mL) of melted fatty acids followed by 1 hour of stirring at 330° C. after each addition.

At the end of the last addition, the crude medium is stirred at 330° C. during an additional hour and the reaction progress is monitored through FTIR.

At the end of the reaction when the intermediate iron complex is not detected anymore through FTIR (absorption bands at 1550 cm-1 and 1408 cm-1), the mixture is allowed to cool down at room temperature and dissolved in 400 mL of CHCl3.

The obtained solution is filtered through a path of 400 g of silica gel followed by elution with 5 liters of CHCl3 in order to remove iron oxide.

The chloroform is evaporated under vacuum and the crude product is dried overnight under 10 mbar at 50° C. to obtain 207 g of ketone (which contains 167 g (0.475 mole) of product generated through ketonization of the 200 g of fatty acids in addition to the 40 g of fatty ketones that have been dispensed initially in the reactor) as a light brown wax corresponding to a crude yield of 98%.

Analysis of the crude shows a GC purity of 96% (impurities being mainly hydrocarbons) with the following composition for the ketones cut:

C15: 0.5 wt %, C17: 1.3 wt %, C19: 8.4 wt %, C21: 11.4 wt %, C23: 28.4 wt %, C25: 19.0 wt %, C27: 13.0 wt %, C29: 11.7 wt %, C31: 3.7 wt %, C33: 1.6 wt %, C35: 0.9 wt %.

Example 2

Ketonization of C8-C18 Fatty Acids Cut Using Fe(III) Oxide Fe2O3 as the Catalyst The reaction is carried out under an inert atmosphere of argon.

In a 750 mL reactor equipped with a mechanical stirrer, a Dean-Stark apparatus to trap water generated during the reaction and an addition funnel, are dispensed 40 g of product C15-C35 ketones (made through a previous ketonization of the starting C8-C18 fatty acids) and 9.74 g (0.060 mole) of Fe2O3.

The addition funnel is filled with 200 g (0.970 mole) of melted fatty acids (C8: 7 wt %, C10: 8 wt %, C12: 48 wt %, C14: 17 wt %, C16: 10 wt %, C18: 10 wt %).

The reaction mixture is then heated at 330° C. under stirring (500 rpm) and 200 g (0.970 mole) of the melted fatty acids is slowly introduced into the reactor such that the temperature of the reaction medium doesn't fall down below 320° C. (for example with an addition flow rate of around 25 g fatty acids/hour).

Practically this can be done through the successive slow additions (1 hour per addition) of 4 portions of 50 g (60 mL) of melted fatty acids with 1 hour of stirring at 330° C. between each addition.

At the end of the last addition, the crude medium is stirred at 330° C. during 0.5 hour and the reaction progress is monitored through FTIR.

At the end of the reaction when the intermediate iron complex is not detected anymore through FTIR (absorption bands at 1550 cm-1 and 1408 cm-1), the mixture is allowed to cool down at room temperature and dissolved in 300 mL of CHCl3.

The obtained solution is filtered through a path of 400 g of silica gel followed by elution with 3 liters of CHCl3 in order to remove iron oxide.

The chloroform is evaporated under vacuum and the crude product dried overnight under 10 mbar at 50° C. to obtain 204 g of ketone (164 g (0.475 mole) of product generated through ketonization of the 200 g of fatty acids in addition to the 40 g of fatty ketones that have been dispensed initially in the reactor) as a light brown wax corresponding to a crude yield of 96%.

Analysis of the crude shows a GC purity of 97% (impurities being mainly alkanes) with the following composition for the ketones cut:

C15: 0.5 wt %, C17: 1.2 wt %, C19: 8.4 wt %, C21: 11.2 wt %, C23: 28.6 wt %, C25: 19.1 wt %, C27: 13.2 wt %, C29: 11.4 wt %, C31: 3.5 wt %, C33: 1.5 wt %, C35: 0.7 wt %.

Example 3 (Comparative)

Ketonization of C8-C18 Fatty Acids Cut Using Magnetite Fe3O4 as the Catalyst with Direct Introduction of Entire Amount of Fatty Acids to be Converted and Without Initial Introduction of Ketone The reaction is carried out under an inert atmosphere of argon.

In a 500 mL round bottom flask equipped with a mechanical stirrer and a Dean-Stark apparatus to trap water generated during the reaction, 100 g (0.480 mole) of melted fatty acids (C8: 7 wt %, C10: 8 wt %, C12: 48 wt %, C14: 17 wt %, C16: 10 wt %, C18: 10 wt %) and 4.7 g (0.020 mole) of magnetite Fe3O4 are dispensed.

The mixture is then allowed to stir under reflux (330° C. ordered) during 8 hours. The reaction media temperature increases progressively over the course of the reaction from 250° C. (beginning) to 303° C. after 8 hours of stirring. Importantly generation of water is observed and at the end of the reaction GC analysis (normalization) shows approximately that the conversion of fatty acids is around 40% (significant amounts of fatty acids remaining), the selectivity of ketone formation is about 55% and the approximate yield of ketones is only 23%.

Example 4 (Comparative)

Ketonization of Lauric Acid Using Fe as the Pre-Catalyst with Direct Introduction of Entire Amount of Fatty Acids to be Converted and Without Initial Introduction of Ketone Lauric acid was mixed with 12.5 mol % of iron powder and heated to 298° C. (boiling point of lauric acid) and kept at this temperature for 5 hours. Formation of complex is observed through FTIR analysis.

Thereafter the composition of the reaction product was determined. The yield of 12-tricosanone was only 18% and a significant amount of undecane was formed (8%). Furthermore, substantial amounts of unreacted lauric acid were still present (total conversion of lauric acid is 46%).

The invention claimed is:

1. A process P for synthesizing an internal ketone K1 by decarboxylative ketonization reaction of a fatty acid, a fatty acid derivative or a mixture thereof in a liquid phase with a metal compound as catalyst in a reaction medium, wherein a ketone K2 at liquid state, where the difference between the boiling point of K1 and K2 is less than or equal to 80° C., is introduced into the reaction medium.

2. The process according to claim 1, wherein the ketone K2 has a boiling point of at least 310° C.

3. The process according to claim 1-or-2, wherein the difference between the boiling point of the ketone K1 and the boiling point of the ketone K2 is equal to or lower than 10° C.

4. The process according to claim 1, wherein the catalysis is homogeneous catalysis, that is to say that in the reaction conditions an intermediate metal carboxylate salt is formed through the initial reaction between the fatty acid or its derivative with the metal compound and this intermediate salt is substantially soluble in the reaction medium.

5. The process according to claim 1, wherein the metal compound is an iron oxide.

6. The process according to claim 1, wherein, the molar ratio of fatty acid, fatty acid derivatives or mixtures thereof to metal is in the range of from 6:1 to 99:1.

7. The process according to claim 1, wherein the ketone K2 is identical to ketone K1 and wherein the ketone K2 introduced is originated from a previous process P for synthesizing a ketone K1 by decarboxylative ketonization reaction of a fatty acid, a fatty acid derivative or a mixture thereof.

8. The process according to claim 1, wherein a fatty acid is used as starting material and the fatty acid is at least one carboxylic acid having at least 10 carbon atoms.

9. The process according to claim 1, wherein one and only one fatty acids is used as a starting material.

10. The process according to claim 1, comprising the steps of:
introducing in any order at least part of the ketone K2 at liquid state, at least part of the metal compounds, at least part of the fatty acid, fatty acid derivative or mixture thereof into a reactor in order to synthesize the ketone K1, said reactor optionally containing before said introduction, a part of the metal compounds, and/or a part of the fatty acid, fatty acid derivative or mixture thereof and/or a part of the ketone K2 and/or a part of the ketone K1,
recovering the ketone K1 optionally together with the ketone K2
optionally recycling at least part of the ketone K1 and/or ketone K2 and/or at least part of the metal compounds to step a).

11. The process according to claim 10, wherein step a) comprises the steps:
a1) introducing at least part of the ketone K2 at liquid state, and at least part of the metal compounds into a reactor, said reactor optionally containing before said introduction, a part of the metal compounds, and/or a part of the ketone K2 and/or a part of the ketone K1, and said reactor being totally free of fatty acid(s) and fatty acid derivatives(s),
a2) introducing the fatty acid, fatty acid derivative or mixture thereof into the reactor, optionally with a part of the metal compounds, and/or
a part of the ketone K2 and/or,
a part of the intermediate metallic carboxylate salts obtained by reacting metal compounds and the fatty acids or fatty acid derivatives before decomposition to form the ketone K1.

12. The process according to claim 11, wherein at step a2), the fatty acid, fatty acid derivative or mixture thereof is introduced sequentially or continuously into the reactor.

13. A method comprising reacting an internal ketone K1 synthesized by the process according to claim 1 with at least one reagent to form an end compound having a twin-tail structure.

14. A method comprising reacting an internal ketone K1 synthesized by the process according to claim 1 with at least one reagent to form an end compound having a Gemini structure.

15. A method M for the preparation of a compound from an internal ketone K1, said method M comprising:
synthesizing the internal ketone K1 by the process P according to claim 1, and
causing the internal ketone K1 to react in accordance with a single or multiple chemical reaction scheme involving at least one reagent other than the internal ketone K1,
wherein at least one reagent is selected from the group consisting of ammonia, primary or secondary amines, mixtures of at least one aldehyde with ammonia or with at least one primary or secondary amine and alkylating agents;
wherein an optional intermediate is formed, the optional intermediate being selected from the group consisting of twin tail primary, secondary or tertiary amines, twin-tail tertiary amines themselves substituted by one or two primary, secondary or tertiary amino groups, internal ketone monoamines and internal ketone diamines; and
wherein at least one product of the chemical reaction scheme is the end compound that is not further caused to be chemically converted into another compound.

16. The process according to claim 1, wherein the ketone K2 is similar to the internal ketone K1 in that the difference between the boiling point of the internal ketone K1 and the boiling point of the ketone K2 is equal to or lower than 80° C.

17. The process according to claim 1, wherein a fatty acid is used as starting material and the fatty acid is selected from the group consisting of caprylic acid, capric acid, lauric acid, myristic acid, palmitic acid, stearic acid and mixtures thereof.

18. The process according to claim 17, wherein the fatty acid is a C8-C18 fatty acids cut.

19. A process P for synthesizing an internal ketone K1 by decarboxylative ketonization reaction of a fatty acid, a fatty acid derivative or a mixture thereof in a liquid phase with a metal compound as catalyst in a reaction medium, wherein a ketone K2 at liquid state is introduced into the reaction medium.

20. The process according to claim 19 wherein the ketone K2 has a boiling point of at least 270° C.

21. The process according to claim 20 wherein the ketone K2 has a boiling point of at least 310° C.

22. The process according to claim 21, wherein the ketone K2 is selected from the group consisting of 8-octadecanone, benzoin, 10-nonadecanone, anthraquinone, 12-tricosanone, trans,trans-dibenzylideneacetone, 13-pentacosanone, 14-heptacosanone, 16-hentriacontanone, 18-pentatriacontanone, 19-heptatriacontanone and 20-nonatriacontanone.

23. The process according to claim 19, wherein the ketone K2 is identical to internal ketone K1 and the ketone K2 introduced is originated from a previous process P for synthesizing an internal ketone K1 by decarboxylative ketonization reaction of a fatty acid, a fatty acid derivative or a mixture thereof.

24. The process according to claim 23, wherein the ketone K2 is one or more ketones of formula (I)

(I)

wherein Rn and Rq independently represent an aliphatic group, and the number of carbon atoms of Rn and of Rq, as herein represented by a couple (n,m), is selected from the group consisting of (9,9), (11,11), (13,13), (15,15), (17,17), (19,19), (21,21), (23,23), (25,25), (27,27), (7,9), (7,11), (7,13), (7,15), (7,17), (7,19), (7,21), (7,23), (7,25), (7,27); (9,11), (9,13), (9,15), (9,17), (9,19), (9,21), (9,23), (9,25), (9,27), (11,13), (11,15), (11,17), (11,19), (11,21), (11,23), (11,25), (11,27), (13,15), (13,17), (13,19), (13,21), (13,23), (13,25), (13, 27), (15,17), (15,19), (15,21), (15,23), (15,25), (15,27), (17,19), (17,21), (17,23), (17,25), (17,27), (19,21), (19,23), (19,25), (19,27), (21,23), (21,25), (21,27), (23,25), (23,27) and (25,27).

25. The process according to claim 19 wherein a fatty acid is used as starting material and the fatty acid is at least one carboxylic acid having at least 10 carbon atoms or is a C8-C18 fatty acids cut.

* * * * *

UNITED STATES PATENT AND TRADEMARK OFFICE
CERTIFICATE OF CORRECTION

PATENT NO. : 11,091,417 B2
APPLICATION NO. : 16/326460
DATED : August 17, 2021
INVENTOR(S) : Olivier Back et al.

Page 1 of 1

It is certified that error appears in the above-identified patent and that said Letters Patent is hereby corrected as shown below:

In the Claims

Column 52, Claim 3, Line 44, the term "claim 1-or-2" should read -- claim 1 --.

Column 54, Claim 24, Line 48 and 50, the word "Rq" should read -- Rm --.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*